(12) United States Patent
Ghodsian

(10) Patent No.: US 12,364,408 B2
(45) Date of Patent: *Jul. 22, 2025

(54) SYSTEM AND METHOD FOR CHILD-BEARING MONITORING AND ASSISTANCE

(71) Applicant: Kamran Ghodsian, Newport Beach, CA (US)

(72) Inventor: Kamran Ghodsian, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/485,061

(22) Filed: Oct. 11, 2023

(65) Prior Publication Data
US 2024/0099600 A1 Mar. 28, 2024

Related U.S. Application Data

(63) Continuation of application No. 17/083,883, filed on Oct. 29, 2020, now Pat. No. 11,793,416, which is a
(Continued)

(51) Int. Cl.
*A61B 5/00* (2006.01)
*A61B 1/303* (2006.01)
*A61B 5/03* (2006.01)

(52) U.S. Cl.
CPC .............. *A61B 5/035* (2013.01); *A61B 1/303* (2013.01); *A61B 5/6853* (2013.01);
(Continued)

(58) Field of Classification Search
CPC ....... A61B 5/035; A61B 1/303; A61B 5/6853; A61B 5/6875; A61B 2562/0247;
(Continued)

(56) References Cited

U.S. PATENT DOCUMENTS 4,901,735 A * 2/1990 von Berg ............... A61B 5/035 600/561
4,944,307 A * 7/1990 Hon ....................... A61B 5/035 600/561
(Continued)

FOREIGN PATENT DOCUMENTS

CN 203234767 U 10/2013
WO WO 2022/093867 A1 5/2022

OTHER PUBLICATIONS

Cervical Ripening Balloon with Stylet, Cook Medical Brochure, Sep. 2019.

*Primary Examiner* — May A Abouelela
(74) *Attorney, Agent, or Firm* — Knobbe, Martens, Olson & Bear, LLP

(57) ABSTRACT

The invention is generally a system, apparatus, and method for monitoring and measuring a change in intrauterine pressure without rupturing the amniotic sac. A catheter is coupled to a pressure sensing module. The pressure sensing module is configured with a chamber that is in fluid communication with a balloon of the catheter. The chamber includes a pressure-sensing membrane coupled to sensing circuitry. The sensing circuitry is configured to detect a pressure applied to the pressure-sensing membrane and communicate the condition to a monitor of the system. Methods include inserting the catheter through the cervix so that the balloon may be inflated and situated in the lower segment of the uterus, resting against the amniotic sac. Because the balloon of the catheter is in fluid communication with the pressure-sensing membrane, pulsations of the amniotic sac will be sensed by the sensing circuitry of the pressure sensing module.

17 Claims, 14 Drawing Sheets

Related U.S. Application Data continuation of application No. 16/367,132, filed on Mar. 27, 2019, now abandoned.

(52) U.S. Cl.
CPC ..... *A61B 5/6875* (2013.01); *A61B 2562/0247* (2013.01); *A61B 2562/0271* (2013.01)

(58) Field of Classification Search
CPC ........ A61B 2562/0271; A61B 5/02411; A61B 5/344; A61B 2503/02; A61B 5/02055; A61B 5/6885
See application file for complete search history.

(56) References Cited

U.S. PATENT DOCUMENTS

| | | | | |
|---|---|---|---|---|
| 5,104,377 | A * | 4/1992 | Levine | A61M 25/1011 604/100.01 |
| 5,209,754 | A * | 5/1993 | Ahluwalia | A61B 17/4241 606/1 |
| 5,300,023 | A * | 4/1994 | Lowery | A61M 25/0119 604/271 |
| 5,344,402 | A | 9/1994 | Crocker | |
| 5,566,680 | A * | 10/1996 | Urion | A61B 5/035 600/561 |
| 5,573,007 | A * | 11/1996 | Bobo, Sr. | A61B 5/031 600/587 |
| 5,634,459 | A | 6/1997 | Gardosi | |
| 5,718,685 | A | 2/1998 | Roewer et al. | |
| 5,876,357 | A * | 3/1999 | Tomer | A61B 5/1076 600/587 |
| 5,947,991 | A * | 9/1999 | Cowan | A61M 25/1002 606/191 |
| 5,951,497 | A * | 9/1999 | Wallace | A61B 5/035 600/176 |
| 5,984,879 | A * | 11/1999 | Wallace | A61B 5/035 600/587 |
| 5,993,395 | A * | 11/1999 | Shulze | A61B 5/0215 73/706 |
| 6,024,753 | A * | 2/2000 | Claren | A61B 17/12099 604/515 |
| 6,104,941 | A | 8/2000 | Huey et al. | |
| 6,434,418 | B1 | 8/2002 | Neal et al. | |
| 6,554,780 | B1 * | 4/2003 | Sampson | A61B 18/00 600/560 |
| 6,648,842 | B2 * | 11/2003 | Horkel | A61B 17/42 606/119 |
| 6,890,321 | B2 | 5/2005 | Luther et al. | |
| 7,105,007 | B2 * | 9/2006 | Hibler | A61M 29/02 606/196 |
| 7,220,252 | B2 * | 5/2007 | Shah | A61M 25/1027 604/101.02 |
| 7,850,625 | B2 * | 12/2010 | Paltieli | G06T 7/12 600/443 |
| 8,343,078 | B2 * | 1/2013 | Toth | A61B 18/18 600/560 |
| 8,394,037 | B2 * | 3/2013 | Toth | A61B 18/18 606/41 |
| 8,585,616 | B2 * | 11/2013 | Swann | A61B 17/12136 604/93.01 |
| 8,585,643 | B2 | 11/2013 | Vo et al. | |
| 10,022,497 | B2 * | 7/2018 | Burmaster | F04B 11/0033 |
| 10,252,026 | B2 | 4/2019 | Khalaj | |
| 11,071,481 | B2 | 7/2021 | Dorsey et al. | |
| 11,793,416 | B2 | 10/2023 | Ghodsian | |
| 2001/0047138 | A1 | 11/2001 | Kokate | |
| 2002/0082634 | A1 * | 6/2002 | Kammerer | A61M 25/1002 606/193 |
| 2002/0082635 | A1 * | 6/2002 | Kammerer | A61M 25/1029 606/193 |
| 2004/0116955 | A1 * | 6/2004 | Foltz | A61M 31/00 606/193 |
| 2004/0127932 | A1 * | 7/2004 | Shah | A61M 25/1029 606/193 |
| 2005/0055043 | A1 * | 3/2005 | Foltz | A61M 29/02 606/193 |
| 2005/0240211 | A1 * | 10/2005 | Sporri | A61M 25/1002 606/193 |
| 2006/0058831 | A1 | 3/2006 | Atad | |
| 2006/0271092 | A1 | 11/2006 | Reed et al. | |
| 2007/0015994 | A1 * | 1/2007 | Hong | A61B 8/485 600/407 |
| 2007/0066990 | A1 * | 3/2007 | Marsella | A61M 29/02 606/193 |
| 2007/0250104 | A1 * | 10/2007 | Condrea | A61M 25/1011 606/193 |
| 2007/0288051 | A1 * | 12/2007 | Beyer | A61M 29/02 606/193 |
| 2008/0027421 | A1 * | 1/2008 | Vancelette | A61B 18/02 607/105 |
| 2008/0245371 | A1 | 10/2008 | Gruber | |
| 2008/0319472 | A1 * | 12/2008 | Shelley | A61M 29/02 606/193 |
| 2009/0204099 | A1 | 3/2009 | Feloney | |
| 2010/0087798 | A1 | 4/2010 | Adams et al. | |
| 2010/0145224 | A1 * | 6/2010 | Lee | A61M 25/10 600/562 |
| 2011/0124980 | A1 * | 5/2011 | Hansson | A61B 5/032 600/301 |
| 2011/0152722 | A1 * | 6/2011 | Yackel | A61B 18/082 600/587 |
| 2012/0116217 | A1 * | 5/2012 | Lee-Sepsick | A61M 5/00 600/431 |
| 2012/0130272 | A1 * | 5/2012 | Layton | A61B 5/4325 600/560 |
| 2012/0316460 | A1 * | 12/2012 | Stout | A61B 5/6853 600/561 |
| 2013/0035574 | A1 * | 2/2013 | Anand | A61M 5/16804 604/35 |
| 2013/0204125 | A1 * | 8/2013 | Chang | A61M 25/1002 604/98.01 |
| 2013/0231584 | A1 | 9/2013 | Burnett et al. | |
| 2013/0267868 | A1 * | 10/2013 | Connors | A61M 25/10 600/561 |
| 2014/0024965 | A1 * | 1/2014 | Layton | A61M 13/003 600/560 |
| 2014/0031634 | A1 * | 1/2014 | Swann | A61B 17/12099 600/300 |
| 2014/0221732 | A1 * | 8/2014 | Dayton | A61M 25/00 604/500 |
| 2015/0126990 | A1 | 5/2015 | Sharma et al. | |
| 2015/0164401 | A1 * | 6/2015 | Toth | A61B 5/0538 606/41 |
| 2015/0342641 | A1 * | 12/2015 | Belfort | A61B 17/12099 606/193 |
| 2016/0135740 | A1 | 5/2016 | Ghaffari et al. | |
| 2016/0183977 | A1 * | 6/2016 | Marshburn | A61B 17/4241 606/191 |
| 2016/0262642 | A1 | 9/2016 | Glott et al. | |
| 2016/0270707 | A1 | 9/2016 | Atlee et al. | |
| 2016/0310707 | A1 | 10/2016 | Ghodsian | |
| 2017/0086746 | A1 * | 3/2017 | Ofek | A61B 5/746 |
| 2017/0160175 | A1 * | 6/2017 | Al-Mayah | A61B 5/6853 |
| 2017/0215798 | A1 | 8/2017 | Lonky | |
| 2018/0049658 | A1 | 2/2018 | Smith | |
| 2018/0214067 | A1 | 8/2018 | Filloux et al. | |
| 2018/0344183 | A1 | 12/2018 | McKinney et al. | |
| 2018/0344250 | A1 | 12/2018 | McKinney et al. | |
| 2019/0008443 | A1 * | 1/2019 | O'Dea | A61B 5/435 |
| 2019/0191985 | A1 | 6/2019 | Magno et al. | |
| 2019/0216401 | A1 * | 7/2019 | Brody | A61M 25/10185 |
| 2019/0366017 | A1 * | 12/2019 | Minahan | A61B 1/018 |
| 2020/0214742 | A1 * | 7/2020 | Whisler | A61B 17/135 |
| 2020/0305742 | A1 | 10/2020 | Ghodsian | |
| 2022/0133166 | A1 | 5/2022 | Ghodsian et al. | |

\* cited by examiner

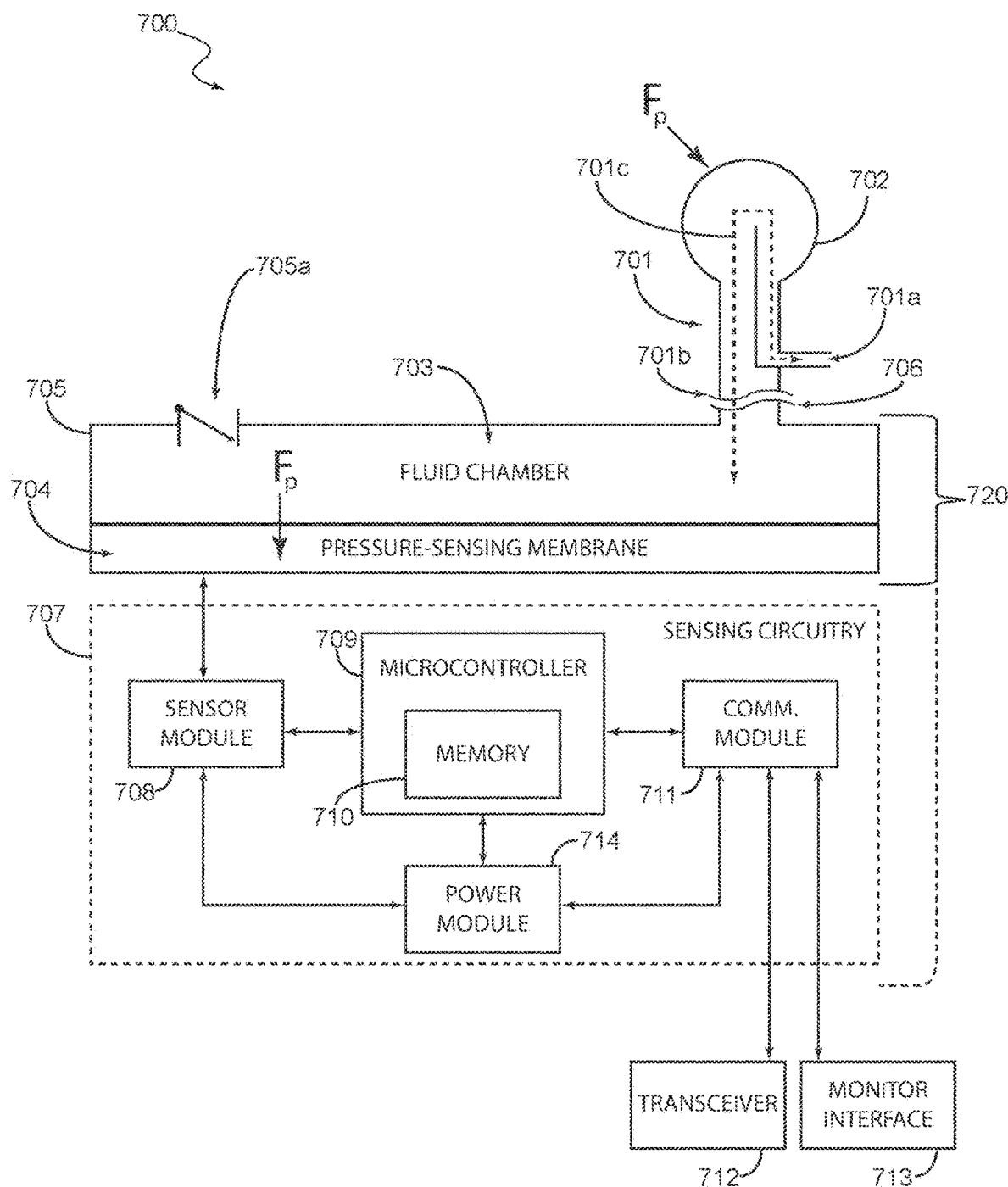

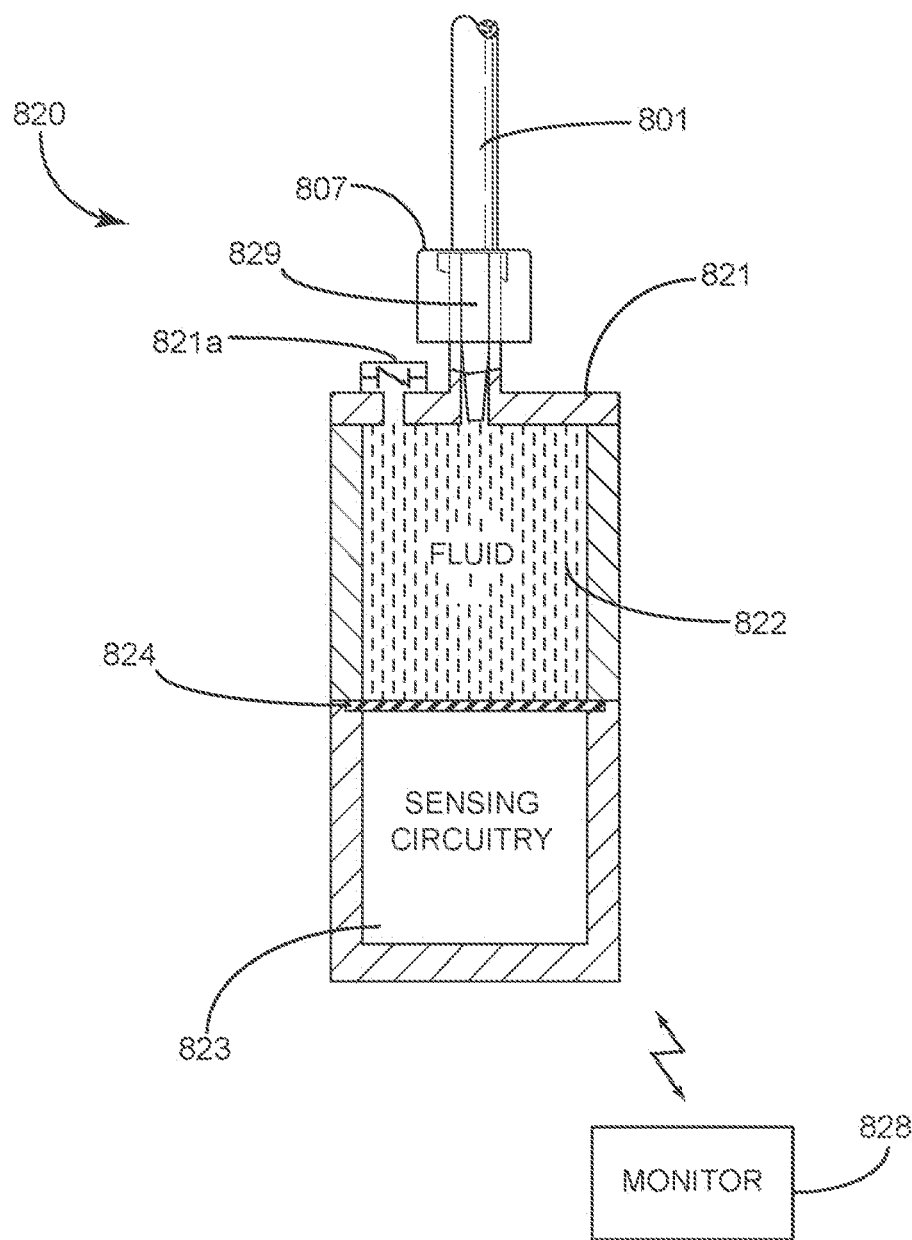

SYSTEM AND METHOD FOR CHILD-BEARING MONITORING AND ASSISTANCE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Technical Field of the Invention

The present invention relates generally to processes of child-birth monitoring and assistance. More specifically, the present invention relates to a system, apparatus, and method for monitoring and measuring a change in intrauterine pressure during labor, without rupturing the amniotic sac.

Copyright And Trademark Notice

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

DESCRIPTION OF THE RELATED ART

There are various reasons to induce labor. For example, when a woman is two or more weeks overdue (postdate), and labor does not start on its own, it may be desirous to induce labor, due to fetal or maternal indications, such as placental dysfunction, pregnancy induced hypertension, Preeclampsia, Diabetes, intrauterine growth restriction, conditions that may jeopardize fetal well-being, or other conditions that may affect the woman's health.

Labor may be induced by causing the cervix to soften and open. For example, the pharmaceutical substance, prostaglandin (PG), leads to local biochemical and biophysical alterations in the cervical region that reduce cervical resistance and induce myometrial contractions. Endocervical, or vaginal application of PG, in a gel form, is presently used for priming the cervix before labor induction and for labor induction. Currently, the Prepidil Gel is applied by intracervical injection using a syringe with a simple cannula. However, it is extremely difficult, if not impossible, to administer 3 ml of gel in a strictly endocervical fashion without applying some of the gel retroamniotically, which may cause side effects to uterine hypercontractility, and may lead to fetal distress.

Intracorporeal labor induction systems of the prior art do not control or measure uterus/amniotic-fluid pressure. By clogging the cervical canal, the existing systems make it hard, if not impossible, to insert a separate pressure measuring instrument into a patient's reproductive system to measure uterus and amniotic-fluid pressures. Furthermore, available uterus/amniotic-fluid pressure measurement devices are inherently inaccurate.

During many labor-inducing procedures, it is desirable to monitor and measure a condition within the uterus. However, known methods often rely on apparatus or devices that are inherently inaccurate and often cause or require the amniotic sac to be ruptured. An advantage of obtaining accurate measurements without breaching the amniotic sac is a decrease in the rate of intrauterine infection for the mother and decrease of infection for the fetus during labor. For example, it is desirable to evaluate the intrauterine pressure during labor before rupturing the amniotic sac. Current methods inadequately address this need.

Accordingly, the prior art inadequately addresses labor monitoring systems that: (i) may induce labor while accurately measuring the uterus and amniotic fluid pressure without rupturing the amniotic sac, (ii) facilitate control of the uterus and amniotic fluid pressure without rupturing the amniotic sac, and (iii) facilitate measuring and or observing a frequency of uterine contractions, without rupturing the amniotic sac.

Therefore, there is a need for a system, apparatus, and method that facilitates the monitoring and measuring of a condition inside the uterus during labor, without rupturing the amniotic sac. It is to these ends that the present invention has been developed.

SUMMARY OF THE INVENTION

To minimize the limitations in the prior art, and to minimize other limitations that will be apparent upon reading and understanding the present specification, the present invention describes a system and method for child-bearing monitoring and assistance.

Generally, the invention involves systems, apparatus, and methods for child-bearing monitoring and assistance but more specifically, a system, apparatus, and method for monitoring and measuring a condition inside the uterus without rupturing the amniotic sac, which in exemplary embodiments employs a pressure sensing module for use with a single or multi-balloon catheter. The single or multi-balloon catheter may be coupled to the pressure sensing module so that a chamber within the pressure-sensing module is in fluid communication with a balloon of the catheter. The chamber includes an impermeable pressure-sensing membrane in communication with a sensor or sensing circuitry. The sensor or sensing circuitry is configured to detect a condition, for example a pressure, applied to the impermeable pressure-sensing membrane and communicate the condition to a monitor of the system. Methods include inserting the catheter through a cervix so that the balloon may be inflated and situated in the lower segment of the uterus, resting against the amniotic sac. Because the balloon of the catheter is in fluid communication with the impermeable pressure-sensing membrane, pulsations of the amniotic sac will be sensed by the sensing circuitry of the pressure sensing module. In this way, a change in intrauterine pressure during labor may be evaluated and monitored without rupturing the amniotic sac.

A system, in accordance with the present invention, for monitoring and measuring a change in intrauterine pressure during labor without rupturing the amniotic sac, may comprise: a catheter configured for manipulation by an operator, the catheter including: a distal end adapted to be placed at least partially inside a cervix of a patient; a uterine balloon situated substantially at the distal end of the catheter adapted to be placed at least partially inside a lower segment of a uterus of the patient; a first port situated at the proximate end of the catheter; a second port situated at the proximate end of the catheter; and a conduit fluidly communicating the first port and the second port to an interior of the uterine balloon, wherein the uterine balloon is inflated by introducing a fluid through the first port; and a pressure sensing module coupled to the second port, the pressure sensing module including an enclosure having a chamber in fluid communication with the uterine balloon via the conduit, a pressure-sensing membrane coupled to the chamber, and a sensing circuitry coupled to the pressure-sensing membrane configured to detect a pressure applied to the uterine balloon of the catheter.

A pressure sensing module, in accordance with the present invention, for monitoring and measuring a change in intrauterine pressure during labor without rupturing the amniotic sac, may include: an enclosure configured to couple to a first port of a catheter, the catheter including: a distal end adapted to be placed at least partially inside a cervix of a patient; a uterine balloon situated substantially at the distal end of the catheter adapted to be placed at least partially inside a lower segment of a uterus of the patient; a second port situated at the proximate end of the catheter; and a conduit fluidly communicating the first port and the second port to an interior of the uterine balloon, wherein the uterine balloon is inflated by introducing a fluid through the first port; a chamber within the enclosure including a chamber port adapted for fluid communication with the uterine balloon via the conduit; a pressure-sensing membrane coupled to the chamber; and a sensing circuitry coupled to the pressure-sensing membrane configured to detect a pressure applied to the uterine balloon of the catheter.

A method, in accordance with practice of the present invention, for monitoring and measuring a change in intra-uterine pressure during labor without rupturing the amniotic sac, may include the steps of: coupling a pressure sensing module to a catheter; inserting the catheter into a vagina and through a cervical canal of a female patient, wherein: a distal end of the catheter is placed inside the cervical canal, and a proximal end of the catheter is kept outside the cervical canal, the catheter including: a uterine balloon in fluid communication with the proximal end and attached at or near the distal end of the catheter, a first port situated at the proximate end of the catheter, a second port situated at the proximate end of the catheter, a conduit fluidly communicating the first port and the second port to an interior of the uterine balloon, and a vaginal balloon situated closer to the proximate end of the catheter than the uterine balloon and adapted to secure the uterine balloon inside the uterus; positioning the uterine balloon at a lower segment of a uterus of the female patient; inflating the uterine balloon from the proximal end and through the catheter by introducing a fluid through a first port of the catheter so that the fluid inflates the balloon and enters a first chamber of the sensing module; positioning the vaginal balloon at an external OS of the cervical canal of the female patient; inflating the vaginal balloon to anchor the uterine balloon inside the lower segment of the uterus so that the uterine balloon rests against an amniotic sac of the female patient; and reading a pressure output from the pressure sensing module.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

BRIEF DESCRIPTION OF THE DRAWINGS

Elements in the figures have not necessarily been drawn to scale in order to enhance their clarity and improve understanding of the various embodiments of the invention. Furthermore, elements that are known to be common and well understood to those in the industry are not depicted in order to provide a clear view of the various embodiments of the invention.

FIG. 7 illustrates a block diagram of an exemplary system employing a pressure sensing module in accordance with some embodiments of the present invention.

FIG. 8C illustrates an exemplary pressure sensing module in accordance with some embodiments of the present invention.

DETAILED DESCRIPTION OF THE PREFERRED EMBODIMENT

Figure 1:
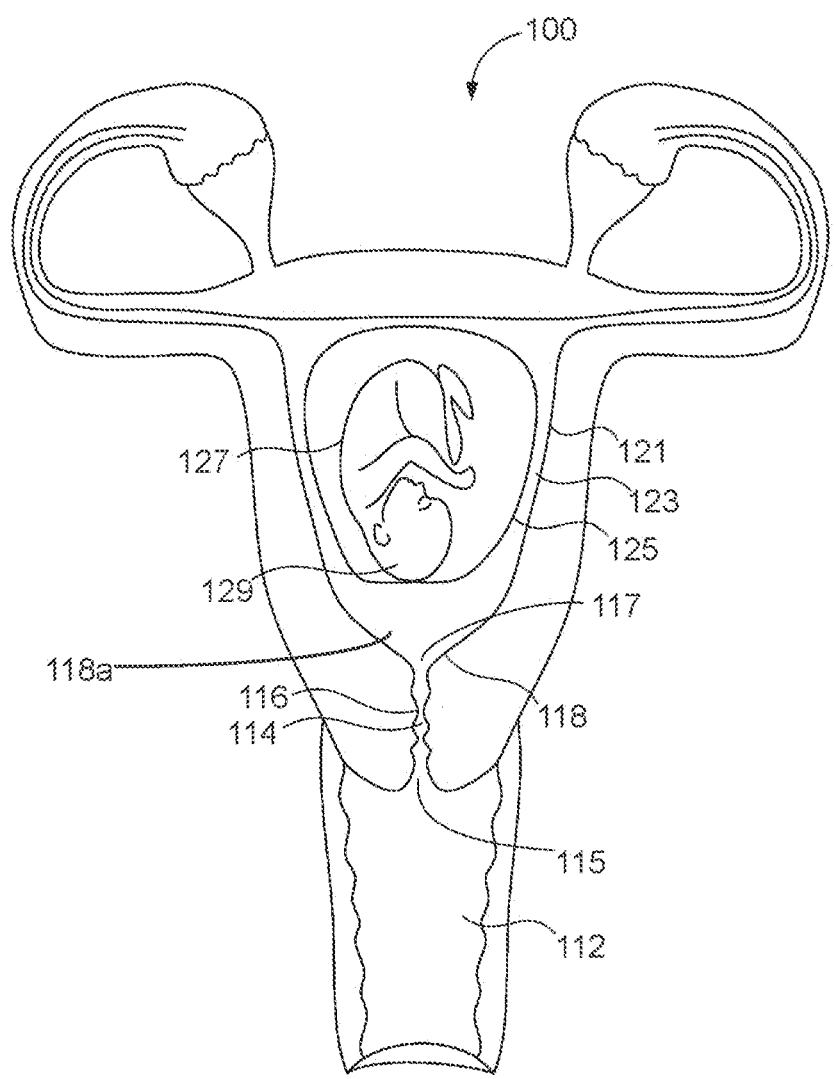
FIG. 1 is a schematic diagram of the women's reproductive system during pregnancy.

In the following discussion that addresses a number of embodiments and applications of the present invention, reference is made to the accompanying drawings, which form a part thereof. Depictions are made, by way of illustration, of specific embodiments in which the invention may be practiced; however, it is to be understood that other embodiments may be utilized, and changes may be made without departing from the scope of the present invention. Wherever possible, the same reference numbers are used in the drawings and the following description to refer to the same or similar elements.

In the following detailed description, numerous specific details are set forth by way of examples in order to provide a thorough understanding of the relevant teachings. However, it should be apparent to those skilled in the art that the present teachings may be practiced without such details. In other instances, well-known structures, components, and/or functional or structural relationship thereof, etc., have been described at a relatively high level, without detail, in order to avoid unnecessarily obscuring aspects of the present teachings.

Throughout the specification and claims, terms may have nuanced meanings suggested or implied in context beyond an explicitly stated meaning. Likewise, the phrase "in one embodiment/example," as used herein, does not necessarily refer to the same embodiment, and the phrase "in another embodiment/example," as used herein, does not necessarily refer to a different embodiment. It is intended, for example, that the claimed subject matter include combinations of example embodiments in whole or in part.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments, whether these features, elements, and/or steps are included or are to be performed in any particular embodiment.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc., may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can include only A, some embodiments can include only B, some embodiments can include only C, and some embodiments can include A, B, and C. The term "and/or" is used to avoid unnecessary redundancy. Similarly, terms such as "a," "an," or "the," again, may be understood to convey a singular usage or to convey a plural usage, depending at least in part upon context. In addition, the term "based on" may be understood as not necessarily intended to convey an exclusive set of facts and may, instead, allow of the existence of additional factors not necessarily expressly described, again, depending at least in part on context.

While exemplary embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the invention or inventions disclosed herein. Accordingly, the following detailed description does not limit the disclosure. Instead, the proper scope of the disclosure is defined by the appended claims.

Generally, the invention involves systems, apparatus, and methods for monitoring and measuring a condition inside the uterus without rupturing the amniotic sac, which in exemplary embodiments employs a pressure sensing module for use with a single or multi-balloon catheter. Coupled to the catheter, a pressure sensing module is configured with a plurality of chambers wherein at least a first of the plurality of chambers is adapted to receive a fluid that is applied via a catheter port and wherein at least a second of the plurality of chambers is adapted to contain air or another fluid separated from the first chamber by a membrane. A sensor coupled to the second chamber may be configured to detect a change in pressure applied to the membrane in order to communicate the pressure change to, for example, a pressure monitor of the system.

In some exemplary embodiments of the present invention, a system for inducing labor may include: a catheter with at least one, two or three balloons (or more) inflatable balloons that are configured to keep the system in an exact position within woman's reproductive system, monitor and/or control pressures inside uterus, exert controllable pressure on the cervical canal walls, stimulate cervical canal, monitor pressures inside cervical canal, and, if desired, administer pharmaceutical substances and/or rupture an amniotic sac.

In some exemplary embodiments of the present invention, a uterine balloon may be positioned at a proximal portion of the uterus, with respect to an operator, adjacent to the cervical internal orifice of the uterus (internal OS). In some embodiments, the uterine balloon may have different shapes so as to, for example, maximize the pressure against the decidua and the external orifice of the uterus (external OS) and to minimize the pressure on the fetal head. In other embodiments, the uterine balloon may have different surface roughness, for example, for anchoring the uterine balloon in place.

In some exemplary embodiments of the present invention, the system may optionally or additionally include a vaginal balloon for positioning in the vagina for applying pressure on the external OS. The combination of a uterine balloon and a vaginal balloon may stabilize the position of the inflatable system within the woman's reproductive system as long as both balloons are inflated.

In some exemplary embodiments of the present invention, the system may optionally or additionally include a cervical balloon for positioning in the cervical canal, shaped so as to maximize the contact area with the cervix. The shape and the surface roughness of the cervical balloon may also be designed in order to maximize cervix contact and stimulation.

In exemplary embodiments, the one or more balloons of the system may stimulate the secretion of hormone by exerting pressure on the proximal decidual surfaces of the uterus and on the cervix, to soften and ripen the cervix, to cause the cervix to dilate, and to induce labor. The balloons, which in some embodiments may have rough external surfaces in order to keep them anchored in place, may be inflated by the operator directly after their insertion, or manually and gradually by the patient.

In some exemplary embodiments of the present invention, various sensors and instruments may be used as part of the system to monitor cervical dilation, fetal well-being, and the woman's conditions. In some embodiments, pharmaceutical substances may also be applied to the cervix canal through a cervical canal portion of the disclosed device.

Turning now to the figures, FIG. 1 is a schematic diagram of the women's reproductive system during pregnancy. More specifically, FIG. 1 illustrates a woman's reproductive system 100 during pregnancy, showing a vagina 112, a cervix 116 forming a cervical canal 114, an ectocervix or external OS 115, an internal OS 117, a uterus 118, an endometrium 121 which is the mucous membrane lining the uterus 118, an amniotic sac 125 containing a fetus 127 having a head 129, and a decidua 123 which is the mucous membrane lining the uterus 118 in preparation for, and during pregnancy.

Figure 2:
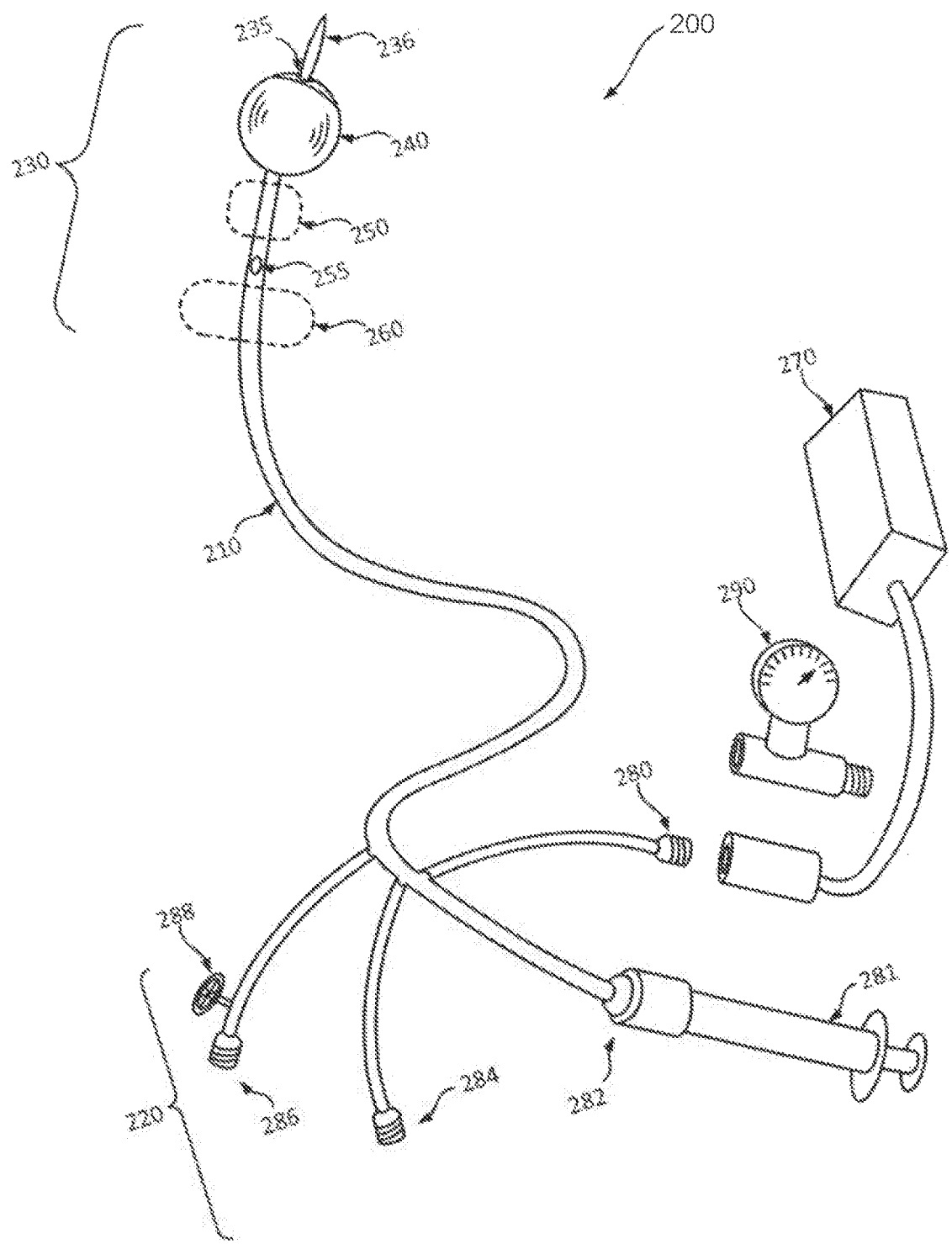
FIG. 2 illustrates an inflatable system in accordance with the present invention.

Turning now to the next figures, FIG. 2 illustrates an inflatable system in accordance with the present invention. More specifically, FIG. 2 schematically illustrates an embodiment of system 200 for cervical dilation, labor induction and uterus and cervical canal pressure monitoring and control. As seen in FIG. 2, system 200 includes a catheter 210 having a proximal end 220 and a distal end 230, with respect to an operator, wherein the distal end 230 enters a woman's reproductive system and the proximal end 220 remains outside her body to be manipulated by an operator/medical staff.

In some exemplary embodiments, catheter 210 may include: (1) a uterine balloon 240 substantially at the distal end 230 and a conduit/tube (not shown) inside the catheter 210, spanning from the proximal end 220 to the distal end 230 and in fluid communication with the uterine balloon 240. In some exemplary embodiments, the catheter 210 may also include a cervical balloon 250, in fluid communication with a cervical-balloon conduit/tube (not shown) inside the catheter 210, spanning from the proximal end 220 to the distal end 230.

As seen in FIG. 2, the location of the cervical balloon 250 on the catheter 210 is closer to catheter's proximal end 220 than the location of the uterine balloon 240 is. The catheter 210 is designed for insertion into the woman's reproductive system, so that the cervical balloon 250 is positioned and inflated within the cervical canal 114. The cervical balloon 250 is designed for applying pressure on the cervix 116. It will be appreciated that the pressure on the cervix 116 may further include pressure on the internal OS 117 and on the external OS 115.

In some embodiments, the inflatable system 200 may include a vaginal balloon 260, in fluid communication with a vaginal-balloon conduit/tube (not shown) inside the catheter 210, spanning from the proximal end 220 to the distal end 230. The vaginal balloon 260 is adapted for positioning within the vagina 1 12, at a distal portion thereof, for pressing against the external cervical OS 115. The one, two or three-balloons of system 200, from catheter 210's distal end 230, may be inserted into a woman's reproductive system 100, prior to inflation of the balloons.

In an exemplary three-balloon inflatable system 200, the uterine balloon 240 and the vaginal balloon 260 are partly operative to anchor the cervical balloon 250 in place and to enhance hormonal secretion by applying pressure on the decidual 123, the internal OS 117, and the external OS 115. At the same time, the cervical balloon 250, anchored within the cervical canal 114, may accelerate cervical dilation, by applying pressure on the cervix 116, and preferably also, the internal OS 117 and on the external OS 115.

In various embodiments the inflatable system 200 may also have openings, such as opening 255, which is in fluid communication with a conduit/tube (not shown) inside the catheter 210, spanning from the proximal end 220 to the distal end 230. Opening 255 is situated on the catheter 210 such that, for example, upon placement in a woman's reproductive system the opening 255 is positioned within the cervical canal 114 and is used to insert pharmaceutical substances into the cervical canal 114.

In accordance with the present invention, the inflation of the balloons of the inflatable system 200 may be performed by a doctor or a midwife (not shown) directly after its insertion. In some exemplary embodiments, the inflation of the balloons of the inflatable system 200 may be performed by the patient via a hand pump 270, in a gradual manner, for example over several hours. Alternatively still, uterine balloon 240 and or vagina balloon 260 may be inflated by the doctor or midwife, while the inflation of the cervical balloon 250 may be performed by the patient, for example, via a hand pump 270. Without limiting the scope of the present invention, pump 270 in FIG. 2 represents any kind of manual or automatic gas or fluid pump suitable for inflating the one or more balloons of catheter 210 of system 200.

Having a pressure sensor at the distal end of the inflatable instrument, inside the uterus and/or cervix canal, has some limitations and disadvantages including: (1) the pressure sensor must be small enough, such as a few millimeters, to fit and/or move inside the instrument, which has to pass through the cervix canal; (2) the pressure sensor must be disposable since the entire intracorporeal part of the system needs to be discarded after use; (3) the sensed pressures need to be transmitted outside the woman's body for recording or display, by wire or wirelessly; and (4) the system will be more expensive and bulkier as a result of the mentioned limitations and disadvantages.

Accordingly, a system for labor induction and monitoring/control in accordance with the present invention will be much smaller, less expensive and simpler if the pressures inside the uterus and/or cervical canal can be transferred to one or more sensors situated outside the woman's body. To do so, a very simple and instantaneous transfer of pressure is possible by using gasses and fluids. However, pressure transfer through a gaseous medium is not as accurate as through incompressible fluids since gasses are compressible and their compressibility varies by temperature and pressure, which introduce undesirable variables into the sensing subsystem. On the other hand, pressure may be accurately sensed at any point of a fluid body without any erroneous effect from the surrounding variables. Therefore, the preferred embodiment of this specification inflates, at least, the uterine balloon by nontoxic incompressible fluids such as water.

In the uterus, as a result of hydraulic principles, the pressure inside the fluid-filled uterine balloon will rapidly come to static equilibrium with the pressures of the amniotic sac and the uterus walls. At such stage, the pressure of the amniotic fluid, the uterine balloon fluid and the pressure on the uterus walls are equal. Hence a sensor outside the woman's body and in fluid contact with the uterine balloon will sense the exact pressure of the uterus/amniotic fluid. The uterus/amniotic fluid pressure may be controllably increased or decreased by inflating or deflating the uterine balloon, respectively. While inflating or deflating the uterine balloon, the exact pressure inside the uterus may also be sensed and observed. With fluid, no wait time is required for pressure equilibrium. A pressure sensing module that may be used with system 200 or other systems in accordance with exemplary embodiments of the present invention, is discussed further below with reference to FIG. 5, FIG. 6A, FIG. 7, and FIGS. SA-SC.

The same is true about a cervical balloon and the monitoring and control of the cervix pressures. In some embodiments, the fluid inside the cervical canal balloon may even be pulsated to further stimulate the canal walls. The pulsation may be caused manually or mechanically. Here also, the cervical balloon itself may be a combination of multiple balloons which may be inflated separately or as a group.

The inflation/deflation of multiple balloons may be controlled together or independently to allow stimulation of the cervical canal with variable pressures across both time and position within the cervical canal. Such an arrangement may be used to create a pressure signal, varying over time and space, to stimulate different regions within the canal at different pressures and at different times, which may be helpful in stimulating dilation more effectively.

For example, if two balloons are employed, their inflation and deflation may be alternated to create a two-point variable pressure signal. In some embodiments, the inflatable system 200 may be coupled with a pressure controller to automatically inflate and deflated the multiple balloons according to a predefined signal pattern chosen by the operator. For example, the pressure controller may have several settings such as sinusoidal pattern, ramped inflation/deflation, and pulsed/rapid inflation/deflation, each of which may be selected by the operator to inflate and deflate the balloons accordingly for different types of stimulation. In multiple balloon embodiments, each balloon may need its own separate micro-tube for independent inflation/deflation, in which the micro-tubes pass through a larger outer tube to allow easy handling and control of the inflatable system, in a manner similar to those shown in FIGS. 3A-3D discussed below.

In general, a vaginal balloon in accordance with the present invention need not be inflated by fluid because it is usually not used to sense or control any pressure; however, if fluid is used to inflate the other balloons, it may be easier to do the same with the vaginal balloon. The vaginal balloon may also consist of more than one balloon controlled as a group or separately in a manner similar to the cervical canal balloons described above.

In exemplary embodiments, at least one of the balloons is inflated by fluid such as water to accurately measure and control the pressure of its surrounding. An increase or decrease of the size of the balloons will increase or decrease, respectively, the pressure of their environment which at the same time can be measured. For example, a small fluid inflation of the uterine balloon 240 enables an accurate measurement of the uterus and amniotic fluid pressures while any increase in the uterine balloon size will increase the uterus and amniotic fluid pressures. Same is true with cervical canal pressure measurement and control. Usually there is no need for measurement and/or control of vaginal pressure and therefore the vaginal balloon may be inflated by air instead of a fluid.

FIG. 2, shows an example system 200 with four connection ports 280, 282, 284, and 286, to which gas and fluid pumps, sensors and gauges, and other instruments may be attached. Each port may be of different kind and use different operating mechanisms. For example, connection port 280 may be closed in its unattached state and be open as long as being connected to any device. Or, for example, port 286 may have a manually operated valve 288.

Therefore, connection port 280, which in this example is assumed to be in fluid communication with uterine balloon 240, may first be connected to a pressure gauge 290 and a fluid pump 270 until the uterine balloon 240 is inflated to a desired pressure or size and subsequently be disconnected from the pump, if needed. In such a case, the uterus pressures can be continuously monitored. If constant monitoring of the pressure is not needed, both the pressure gauge 290 and the fluid pump 270 may be removed and the pressure of uterus be checked at the connection port 280 whenever desired. In some embodiments, the conduit/tube connecting connection port 280 to uterine balloon 240 may even have a separate dedicated port for connecting to sensors and gauges. In yet another example, connection port 280 may be attached to an automated machine for monitoring and/or controlling the pressure of the uterus. In various embodiments, dedicated monitoring ports for each balloon may be connected to a monitoring device(s) while ports, such as port 280, are dedicated to injection, manipulation and/or pumping devices. In these embodiments the pumping device can be a mere syringe 281. There is no need for complicated pumping devices with pressure gauge. Assuming that connection port 284 is in fluid communication with cervical balloon 250, it can be connected to a fluid pulsating device that is capable of controlled fluid pulsation with desired low and high pressures.

If fluid is used to inflate the balloons, there are several ways to eliminate the air in the conduits/tubes. In one embodiment the conduits and the balloons of the system 200 may be manufactured in a collapsed or vacuumed initial form. In other embodiments the connection ports may provide manual release valves to empty the trapped air while inserting fluid into the conduits. Such solutions are known to those skilled in the art and need no further elaboration.

As illustrated in FIG. 2, different devices may be used as a part of such inflatable system 200. In various embodiments the inflatable system 200 may include at least one additional conduit/tube (not shown), having at least one opening 235, to the uterus. The at least one additional conduit/tube is operable for inserting at least one device 236 to the woman's reproductive system. In the embodiment of FIG. 2, the at least one additional tube is operable for inserting the at least one device 236 into the uterus, via the opening 235. Similarly, another conduit/tube may be used for inserting another device into the cervical canal, via a similar opening. In FIG. 2, the at least one device 236 is a device for rupturing the amniotic sac. Device 236 may be operated as a plunger-like device, using a handle at the proximal end 220 of the inflatable system 200. After the puncture, device 236 may be withdrawn from one of the connection ports.

In yet other embodiments, the at least one device 236 may be a sensor, for example, for sensing amniotic-fluid temperature, or for sensing fetal heart-beat, preferably operable via the opening 235 to the uterus. The measurements may be transmitted extracorporeally in a wired or wireless manner.

It will be appreciated that the device 236 may be selected from the group consisting of device for breaking water, a device for sensing amniotic-fluid temperature, a device for sensing fetal heart-beat, a device for measuring an extent of cervical dilation, a device for measuring a frequency of uterine contractility, a device for measuring an intensity of uterine contractility, a device for amnioscopy, a device for fetoscopy, a device for scalp blood pH sampling, and the like.

Alternatively, the at least one device 236 may include a drug form, designed for passive dispensing of a medication. The drug form may be inserted with a syringe 281, and the syringe 281 may then be withdrawn. The passive dispensing of a medication may be by instantaneous release, delayed release, pulsating release, timed release, slow release, or another release form, as known, operable via the opening 235 to the uterus, or via a similar opening(s) to the cervical canal. Device 236 may be electronically-controlled, pre-programmed, or may be wirelessly controlled from an extracorporeal station.

In yet other embodiments, device 236 may include a device for measuring an extent of cervical dilation, operable via an opening to the cervical canal. The measurements may be transmitted extracorporeally by wire or wirelessly. In various embodiments, device 236 may be a combination of several devises and/or sensors.

Figure 3A:
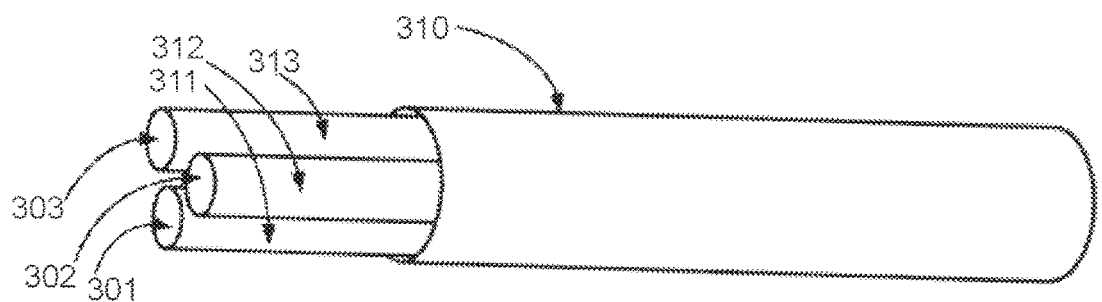
FIG. 3A illustrates an example of possible arrangements for fluid communication from a proximate end to a distal end of an inflatable system in accordance with the present invention.

FIG. 3A-FIG. 3D illustrate several exemplary embodiments of conduits for a catheter in accordance with the present invention. In FIG. 3A, a first tube 310 may include separate conduits 301, 302, and 303 corresponding to separate tubes 311, 312, and 313, all of which reside within a conduit of tube 310. In exemplary embodiments, each of tubes 311, 312, and 313 may connect to a connection port, to a balloon or an opening via their own respective conduits 301, 302, and 303.

Figure 3B:
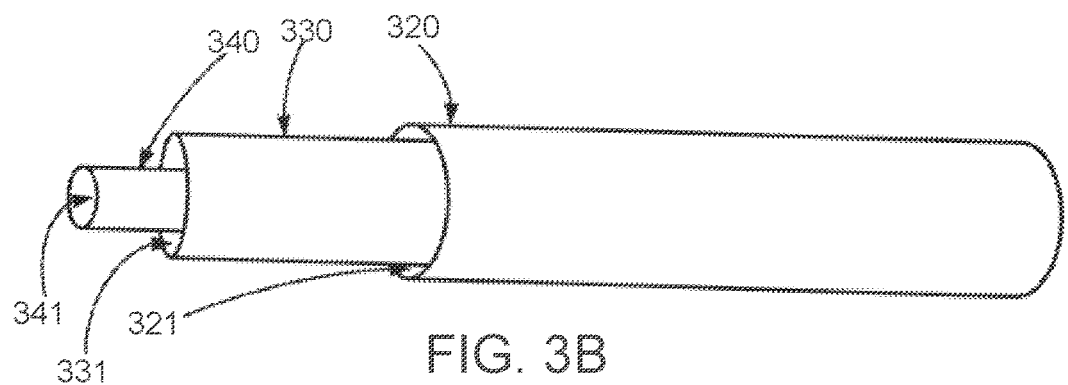
FIG. 3B illustrates an example of possible arrangements for fluid communication from a proximate end to a distal end of an inflatable system in accordance with the present invention.
Figure 3C:
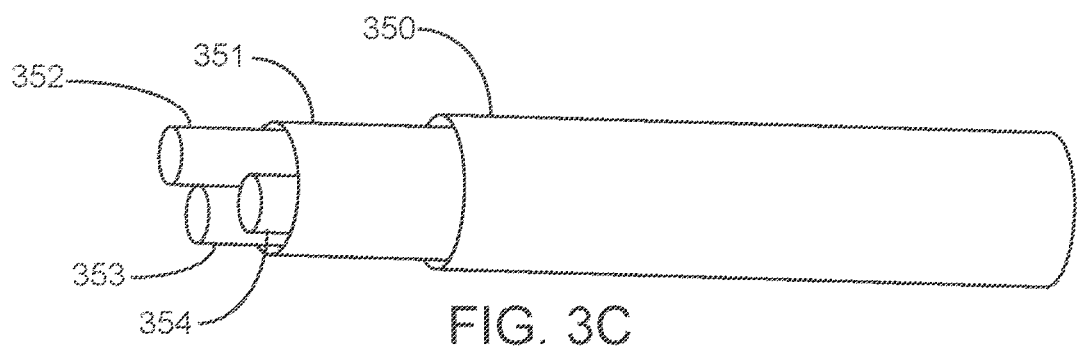
FIG. 3C illustrates an example of possible arrangements for fluid communication from a proximate end to a distal end of an inflatable system in accordance with the present invention.
Figure 3D:
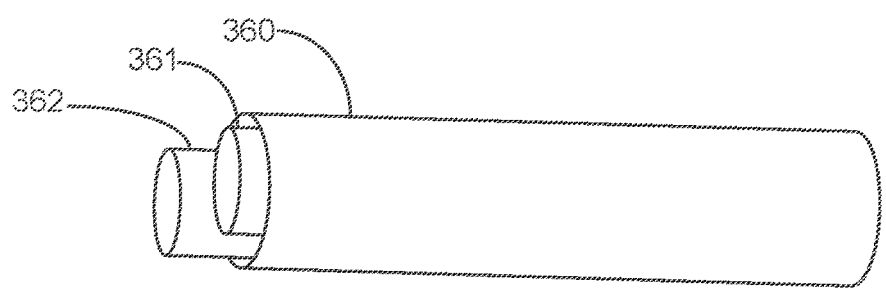
FIG. 3D illustrates an example of possible arrangements for fluid communication from a proximate end to a distal end of an inflatable system in accordance with the present invention.

As will be evident from the following figures, other configurations of tubes and conduits may be possible without deviating or limiting the scope of the present invention. In FIG. 3B, tubes 340 and 330 may be nested within tube 320, each of the tubes providing concentric conduits 341, 331, and 321, respectively. In other embodiments the arrangement of the tubes may be a combination of the arrangements in FIGS. 3A and 3B. For example, and without limiting the scope of the present invention, FIG. 3C shows tube 350 housing tube 351, which in turn houses several tubes 352, 353, and 354. FIG. 3D shows yet another embodiment, in which a single catheter tube may include two smaller tubes with conduits therein, such as tube 360 housing tube 361 and tube 362.

Figure 4:
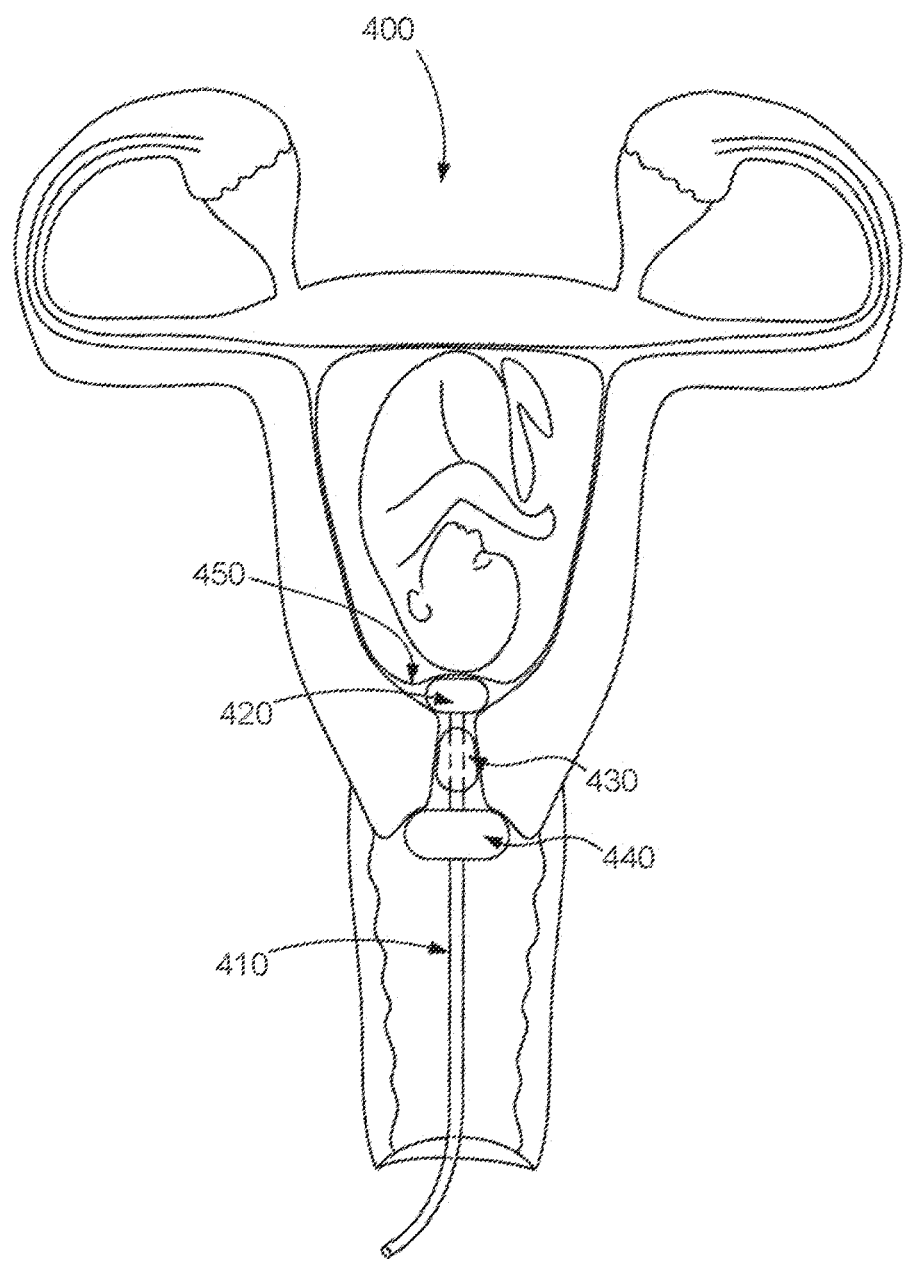
FIG. 4 illustrates an exemplary inflatable system in accordance with the present invention, shown inside a woman's reproductive system.

Turning now to the next figure, FIG. 4 depicts a three-balloon catheter 410 that has been inserted into a woman's reproductive system 400 and subsequently inflated, so that the uterine balloon 420 is in contact with the amniotic sac 450 in the lower segment of the uterus, the cervical balloon 430 is in the cervical canal, and the vaginal balloon 440 is in the distal end of the vagina.

In the example of FIG. 4, the uterine balloon 420 applies pressure on the decidua and the internal OS. The cervical balloon 430 applies pressure on the cervix walls, and the vaginal balloon 440 applies pressure on the external OS. For withdrawal, the balloons are deflated.

As seen from FIG. 4, the uterine balloon 420 is operative partly to separate the amniotic sac 450 from the decidua in the lower segment of the uterus, thereby stimulating endogenous hormone secretion of PG from the decidua. The hormone secretion by the decidua is operative to soften and ripen the cervical canal and induce labor. Similarly, the cervical balloon 430 is operative to stimulate hormone secretion by the cervix. Again, the hormone secretion is operative to soften and ripen the cervical canal and induce labor.

In some embodiments electrocardiogram of the fetus heart may be obtained by temporarily or permanently attaching a desired type and number of electrodes on the surface of the uterine balloon 420, to be directly in contact with the fetus head or indirectly through the amniotic sac, and to send the sensed signals to an extracorporeal EKG or ECG machine, by wire or wirelessly. In some embodiments the electrodes may be a part of or be ingrained in the material of the uterine balloon 420.

Figure 5:
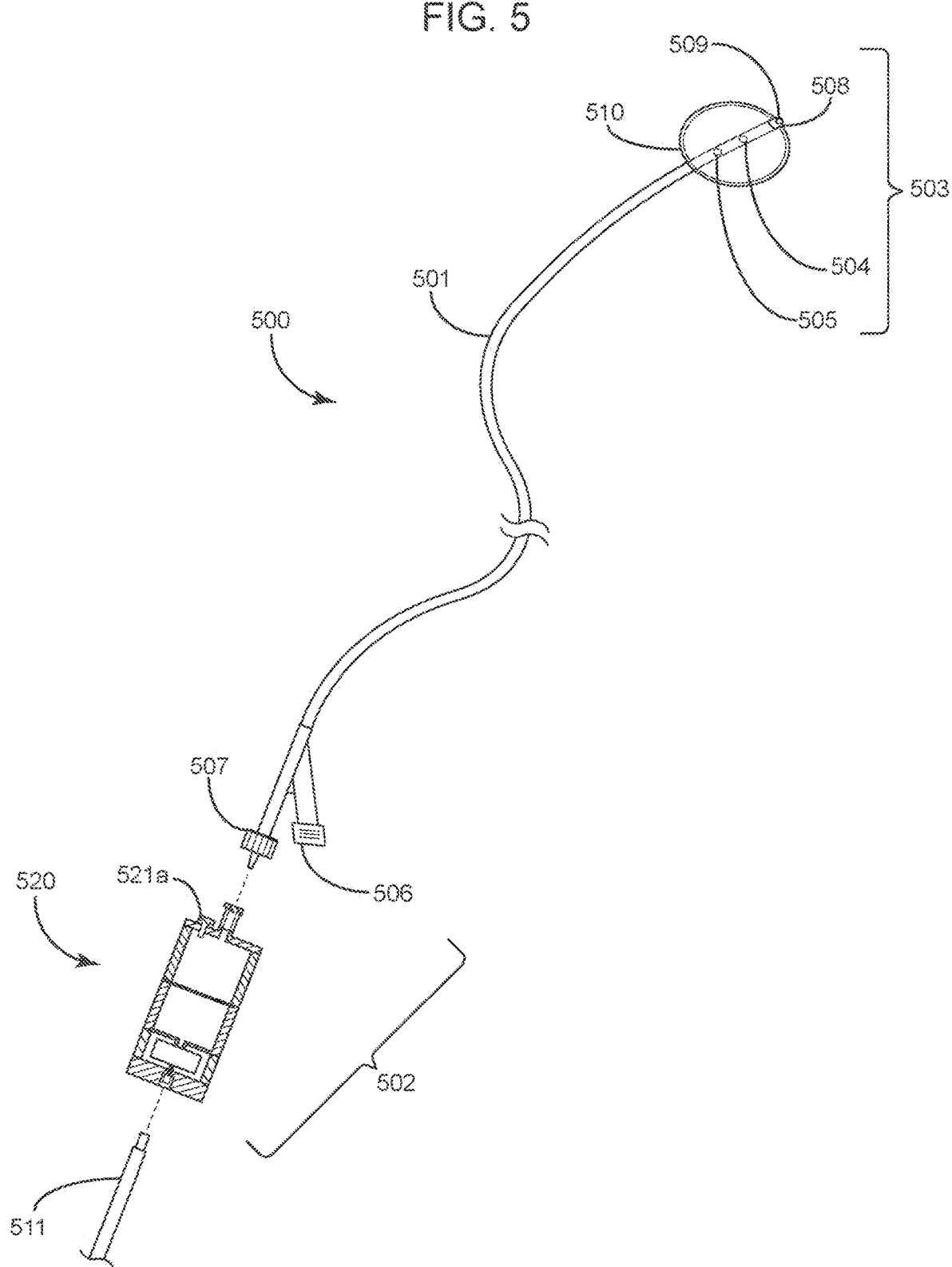
FIG. 5 illustrates an exemplary system in accordance with some embodiments of the present invention that employs a pressure sensing module coupled to a one-balloon catheter.

Turning now to the next figure, FIG. 5 depicts system 500, which includes a catheter 501 having a proximal end 502 and a distal end 503, with respect to an operator, wherein the distal end 503 enters a woman's reproductive system and the proximal end 502 remains outside her body to be manipulated by the operator, such as a physician or medical staff.

In some exemplary embodiments, catheter 501 may include: a single balloon 510 that serves as a uterine balloon, substantially at the distal end 503 of catheter 501; a conduit (not shown) inside the catheter 510, spanning from the proximal end 502 to the distal end 503 in fluid communication with balloon 510 via said conduit with openings 504 and 505; a first port 506 for introducing a fluid into the balloon 510; and a second port 507 coupled directly to a pressure sensing module 520. Catheter 501 may include a tip 508 that is blunt so as to not rupture the amniotic sac or may be alternatively configured to rupture the amniotic sac. The blunt tip 508 may include an opening 509 so that an instrument, such as a temperature transducer or an imaging transducer, may be provided access to the lower segment of the uterus and amniotic sac of a patient via opening 509. Moreover, as will be explained below, in some exemplary embodiments, pressure sensing module 520 may be coupled to an external component such as a sensing device or monitor via communication means 511.

In exemplary embodiments, system 500 includes a catheter 501 configured for manipulation by an operator, the catheter including: a distal end 503 adapted to be placed at least partially inside a cervix of a patient; a balloon 510 situated substantially at the distal end 503 of the catheter 501 adapted to be placed at least partially inside a uterus of the patient; a first port 506 situated at the proximate end of the catheter 501; a second port 507 situated at the proximate end 502 of the catheter 501; and a conduit fluidly communicating the first port 506 and the second port 507 to an interior of the balloon 510, wherein the balloon is inflated by introducing a fluid through the first port 506; and a pressure sensing module 520 coupled to the second port, the pressure sensing module 520 including an enclosure having a first chamber in fluid communication with the conduit, a second chamber in fluid communication with a sensor, and an pressure-sensing membrane separating the first chamber from the second chamber, wherein the pressure sensing module is configured to detect a pressure applied to the balloon of the catheter.

In exemplary embodiments of the present invention, the conduit of the catheter 501 includes: a first conduit communicating the first port 506 to a first opening 504 on the distal end of the catheter situated at the interior of the balloon 510; and a second conduit communicating the second port 507 to a second opening 505 on the distal end of the catheter situated at the interior of the balloon 510.

In exemplary embodiments of the present invention, the first port 506 of the catheter may include a valve configured to prevent a fluid injected through port 506 and into the conduit that fills the balloon 510 from returning back out of port 506. Similarly, a first chamber of pressure sensing module 520 may also include a valve, such as a check-valve or otherwise sealable valve 521a, which allows any air inside the chamber to exit the pressure sensing module as the fluid is received. Once adequately filled, a user may seal the valve 512a in order to maintain the fluid within.

Figure 6A:
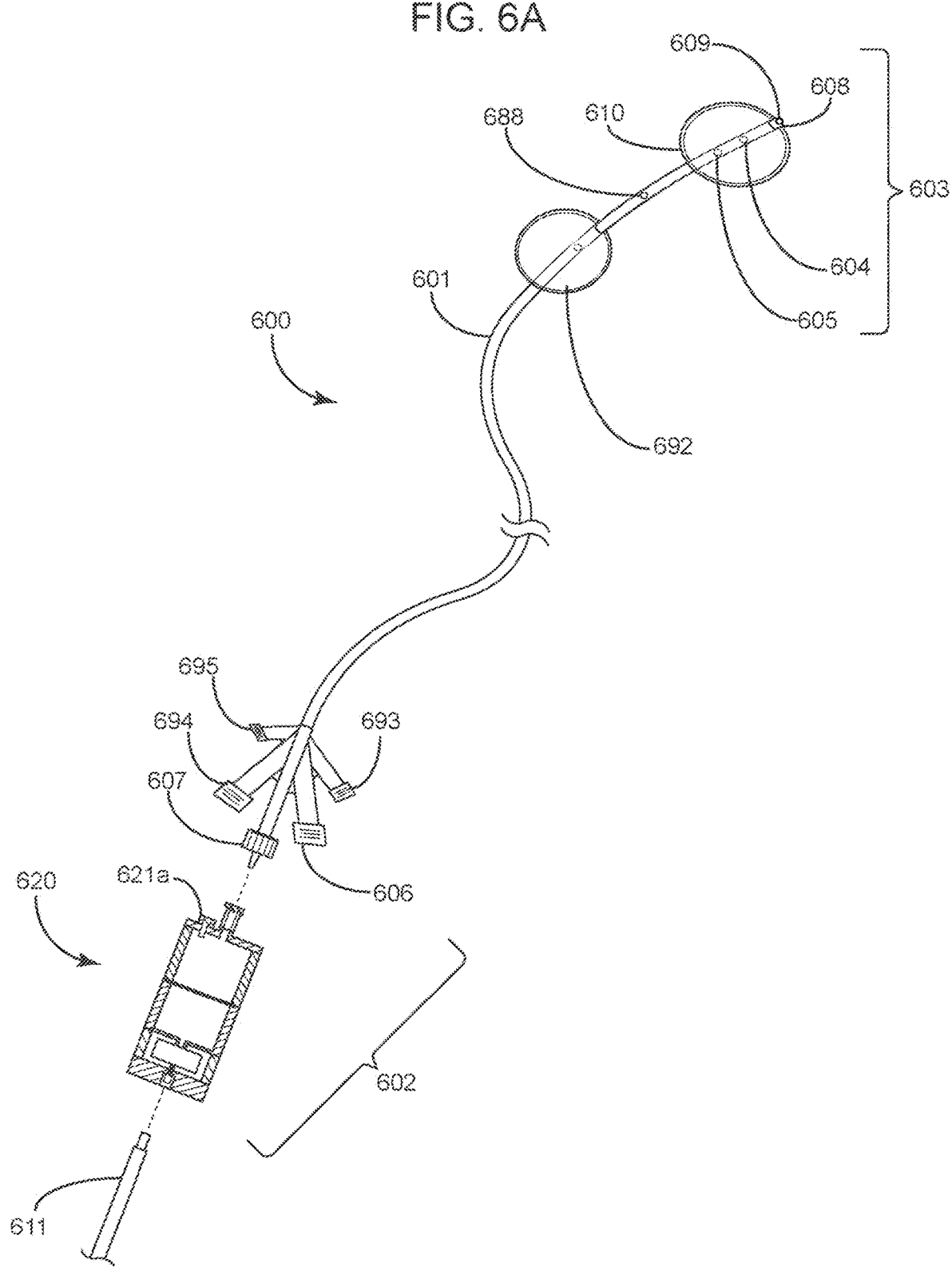
FIG. 6A illustrates an exemplary system in accordance with some embodiments of the present invention that employs a pressure sensing module coupled to a multi-balloon catheter.

Turning now to the next figure, FIG. 6A a similar exemplary embodiment as that shown in FIG. 5, comprising a catheter 601 that may include: a uterine balloon 610 substantially at the distal end 603 and a conduit/tube (not shown) inside the catheter 601, spanning from the proximal end 602 to the distal end 603 and in fluid communication with the uterine balloon 610, and a vaginal balloon 692, in fluid communication with a vaginal-balloon conduit/tube (not shown) inside the catheter 601, spanning from the proximal end 602 to the distal end 603. The vaginal balloon 692, is spaced apparat and situated a distance closer to the proximate end 602 of the catheter 601 so that when catheter 601 is inserted through the cervix of a patient, balloon 610 may be situated at a lower segment of the uterus and balloon 693 may be situated outside of the uterus and against an exterior portion of the cervix anchoring the balloon at or proximate to the external OS 115 of the patient (see also FIG. 9 and related discussion below).

In exemplary embodiments, system 600 includes a catheter 601 configured for manipulation by an operator, the catheter including: a distal end 603 adapted to be placed at least partially inside a cervix of a patient; a balloon 610 situated substantially at the distal end 603 of the catheter 601 adapted to be placed at least partially inside a uterus of the patient; a first port 606 situated at the proximate end of the catheter 601; a second port 607 situated at the proximate end 602 of the catheter 601; and a conduit fluidly communicating the first port 606 and the second port 607 to an interior of the balloon 610, wherein the balloon is inflated by introducing a fluid through the first port 606; and a pressure sensing module 620 coupled to the second port, the pressure sensing module 620 including an enclosure having a first chamber in fluid communication with the conduit, the first chamber including a pressure-sensing membrane in communication with a sensor (see for example FIG. 7, or FIGS. SA-SC), wherein the pressure sensing module is configured to detect a pressure applied to the uterine balloon 610 of the catheter 601. In exemplary embodiments of the present invention, the first port 606 of the catheter may include a valve configured to prevent a fluid injected through port 606 and into the conduit that fills the balloon 610 from returning back out of port 606. Similarly, a first chamber of pressure sensing module 620 may also include a valve, such as a check-valve or otherwise sealable valve 621a, which allows any air inside the chamber to exit the pressure sensing module as the fluid is received. Once adequately filled, a user may seal the valve 621a in order to maintain the fluid within.

As seen in FIG. 6A, the location of the vaginal balloon 692 on the catheter 610 is closer to catheter's proximal end 603 than the location of the uterine balloon 610 is. The vaginal balloon 692 is adapted for positioning within the vagina 112, at a distal portion thereof, for pressing against the external cervical OS 115. The distal portion of the two-balloon catheter of system 600 in such embodiment, from catheter 601's distal end 602, may be inserted into a woman's reproductive system 100, prior to inflation of the balloons.

In an exemplary two-balloon inflatable system 600, the vaginal balloon 692 is at least partly operative to anchor the uterine balloon 692 in place. That is, vaginal balloon 692 will help stabilize uterine balloon 610 so that uterine balloon 610 may rest securely against an unruptured amniotic sac of the patient. In this way, more accurate readings may be obtained. More specifically, when uterine balloon is filled and placed against an unruptured amniotic sac, a pressure change within the unruptured amniotic sac may be detected via the pressure sensing module since any change in pressure within the unruptured amniotic sac will be transferred to the uterine balloon, which is in fluid communication with a pressure sensing membrane of the pressure sensing module 620 (see also FIG. 7). Moreover, as with previously discussed exemplary embodiments, pressure sensing module 620 may be coupled to an external component such as a sensing device or monitor via communication means 611.

In various embodiments, the inflatable system 600 may also have openings, such as opening 688, which is in fluid communication with a conduit/tube (not shown) inside the catheter 601, spanning from the proximal end 602 to the distal end 603. Opening 688 is situated on the catheter 610 such that, for example, upon placement in a woman's reproductive system the opening 688 is positioned within the cervical canal 114 and is used to insert pharmaceutical substances into the cervical canal 114. Similarly, catheter 601 may include a tip 608 that is blunt so as to not rupture the amniotic sac or may be alternatively configured to rupture the amniotic sac. The blunt tip 608 may include an opening 609 so that an instrument, such as a temperature transducer or an imaging transducer, may be provided access to the lower segment of the uterus and amniotic sac of a patient via opening 609.

In accordance with the present invention, the inflation of the balloons of the inflatable system 600 may be performed by a doctor or a midwife (not shown) directly after its insertion. Alternatively, the inflation of the balloons of the inflatable system 600 may be performed by the patient via a hand pump, in a gradual manner, for example over several hours.

Without limiting the scope of the present invention, a pump may include any kind of manual or automatic gas or fluid pump suitable for inflating the one or more balloons of catheter 610 of system 600.

As a person of ordinary skill in the art will appreciate, several conduits within catheter 601 will facilitate the inflation of the vaginal and uterine balloons, as well as the introduction of devices such as a stylet and or instruments that may be desirably introduced through the catheter. For example, and without limiting the scope of the present invention, catheter 601 may include (in addition to the ports mentioned above) several ports 693, 694, and 695. In order to inflate balloon 692, a port 693 may be employed. Furthermore, in order to guide catheter 601 into the desired position, another port 694 may be implemented for inserting a stylet (not shown here but see for example FIGS. 6B-6E). Similarly, an additional port 695 may be used in embodiments in which opening 688 is included in order to provide a means for supplying a pharmaceutical or therapeutic agent via said port 695 through opening 688.

Figure 6B:
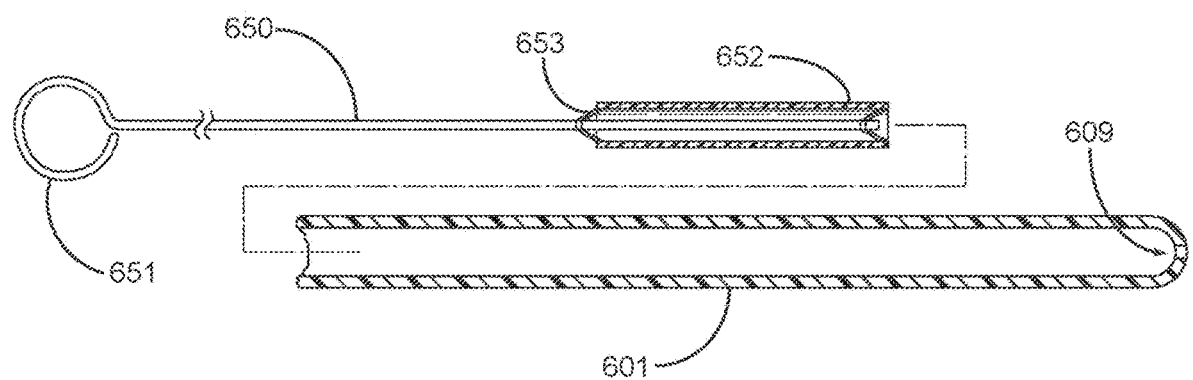
FIG. 6B-6D illustrate an exemplary stylet that may be implemented with some exemplary embodiments of a catheter in accordance with the present invention, which includes a tubular support for facilitating the introduction of other instruments through the catheter.
Figure 6C:
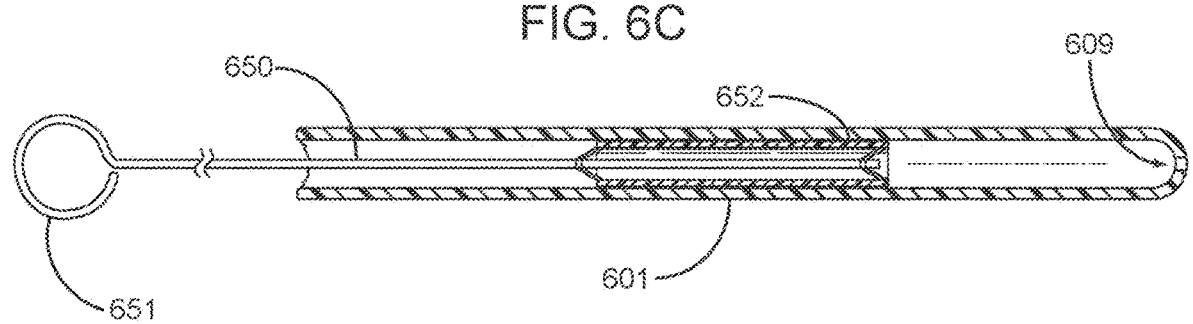
Figure 6D:
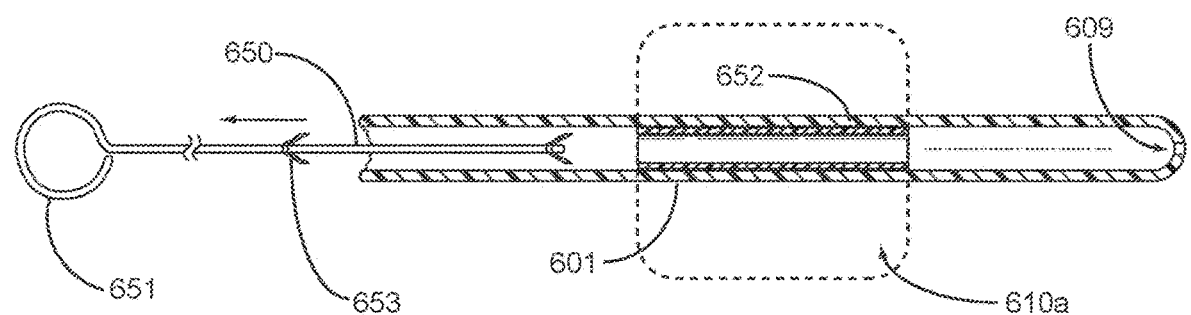

Turning now to the next set of figures, FIGS. 6B-6D illustrate an exemplary stylet that may be implemented with some exemplary embodiments of a catheter in accordance with the present invention, which includes a tubular support for facilitating the introduction of other instruments through the catheter. More specifically, these figures show stylet 650, which includes a handle 651 and a substantially hollow tubular support 652 coupled to stylet 650 via at least one detachable arm 653. The hollow tubular support 652 may be detached or broken off from stylet 650, typically by pressure applied by the operator. It is supposed that braking away the stylet leaves the tubular support inside a conduit of the catheter in order to provide support so that opening 609 may be kept accessible to other devices. As mentioned above, other devices may include a temperature transducer or an imaging transducer, which may be provided access to the lower segment of the uterus and amniotic sac of a patient via opening 609. As illustrated in this set of figures, FIG. 6B shows stylet 650 outside of a conduit of catheter 601; FIG. 6C shows stylet 650 inside the conduit and facilitating a positioning of the tubular support 652 within the conduit; and FIG. 6D shows how once within a desired region (for example a region 610a that may support uterine balloon 610), arms 653 may be broken or snapped off from the tubular support in order to remove stylet 650 and leave the tubular support 652 inside the conduit of catheter 601.

Turning now to the next figure, FIG. 7 illustrates a block diagram of an exemplary system employing a pressure sensing module in accordance with some embodiments of the present invention. More specifically, FIG. 7 depicts system 700 in accordance with some exemplary embodiments of the present invention, which is configured to assist an operator in evaluating an intrauterine pressure during labor before rupturing the amniotic membrane. In some exemplary embodiments, system 700 comprises a catheter 701 having at least one balloon—a uterine balloon 702—in fluid communication with a fluid chamber 703 of a pressure-sensing module 720. The fluid chamber 703 exemplarily includes an impermeable pressure-sensing membrane 704 situated within an enclosure 705 that houses fluid chamber 703. A port 706 of the pressure sensing module 720 communicates a conduit 701c of catheter 701 that fluidly connects balloon 702 to fluid chamber 703. A sensing circuitry 707 is coupled to pressure-sensing membrane 704 and configured to detect a change in pressure applied to balloon 702.

In exemplary embodiments, sensing circuitry 707 typically includes a sensor module 708, a microcontroller 709 having a memory 710 that includes a set of executable instructions for reading sensing data from the sensor module 708, a communications module 711 for transmitting the sensing data to a remote device having a transceiver 712 or directly to a monitor via monitor interface 713, and a power module 714 to supply power to the components of sensing circuitry 707.

In some exemplary embodiments, sensor module 708 may comprise one or more sensors adapted to generate sensing signals concerning a pressure applied to the uterine balloon 702 via sensing a change in pressure applied to pressure-sensing membrane 704. The sensors may include optical sensors, strain gauges, capacitive sensors, Hall Effect sensors, and the like, and may measure stress and/or strain and/or deflection of the pressure-sensing membrane 704.

As may be appreciated from the block diagram, because uterine balloon 702 of catheter 701 is in fluid communication with the pressure-sensing membrane 704, a pressure or force Fp applied to uterine balloon 702 will be transferred to pressure-sensing membrane 704. Accordingly, pulsations of the amniotic sac will be sensed by the sensing circuitry of the pressure sensing module. In this manner, changes in the intrauterine pressure of a patient in labor may be monitored before rupturing the amniotic sac. As briefly mentioned above, an advantage of monitoring intrauterine pressure without rupturing the amniotic sac is a decrease in the risk of intrauterine infections for the mother and fetus during labor that is typically associated with prematurely rupturing the amniotic sac. Moreover, this allows for improved recording of the number of contractions and contraction patters. Further, use of system 700 may further cause the cervix to be diluted and ripen.

In some exemplary embodiments of the present invention, system 700 may include: a catheter 701 configured for manipulation by an operator, the catheter 701 including: a distal end adapted to be placed at least partially inside a cervix of a patient; a uterine balloon 702 situated substantially at the distal end of the catheter 701 adapted to be placed at least partially inside a lower segment of a uterus of the patient; a port 701a situated at a proximate end of the catheter 701; a port 701b situated also at the proximate end of the catheter; and a conduit 701c fluidly communicating port 701a and port 701b to an interior of the uterine balloon 702, wherein the uterine balloon 702 is inflated by introducing a fluid through the port 701a; and a pressure sensing module 720 coupled to port 701b, the pressure sensing module including an enclosure 705 having a fluid chamber 703 in fluid communication with the uterine balloon 702 via the conduit 701c, a pressure-sensing membrane 704 coupled to the fluid chamber 703, and optionally a sensing circuitry 707 coupled to the pressure-sensing membrane 704 configured to detect a pressure applied to the uterine balloon of the catheter. In some exemplary embodiments, the sensing circuitry is external to pressure sensing module 720 (so that the sensing circuitry is housed separately). In some exemplary embodiments, the sensing circuitry is integral with the pressure-sensing module 720 so that the sensing circuitry is housed together with the other components of pressure-sensing module 720, for example wherein enclosure 705 of pressure-sensing module 720 includes a second chamber that houses sensing circuitry 707.

In some exemplary embodiments of the present invention, a pressure sensing module 720 may include: an enclosure 705 configured to couple to port 701b of a catheter 701, wherein the catheter 701 includes: a distal end adapted to be placed at least partially inside a cervix of a patient; a uterine balloon 702 situated substantially at the distal end of the catheter adapted to be placed at least partially inside a uterus of the patient; a port 701a and a port 701b situated at the proximate end of the catheter 701; and a conduit 701c fluidly communicating ports 701a and 701b to an interior of the uterine balloon 702, wherein the uterine balloon 702 is inflated by introducing a fluid through the port 701a. The enclosure 705 houses fluid chamber 703 within the enclosure 705 and includes chamber port 706 adapted to couple with port 701b for achieving fluid communication between fluid chamber 703 and the uterine balloon 702 via the conduit 701c. In exemplary embodiments of the present invention, the port 701a of catheter 701 may include a valve (not shown) configured to prevent a fluid injected through port 701a and into the conduit 701c that fills the balloon 702 from returning back out of port 701a. Similarly, fluid chamber 703 of enclosure 705 may also include a valve, such as a check-valve or otherwise a sealable valve 705a, which allows any air inside fluid chamber 703 to exit as the fluid is received therein. Once adequately filled, a user may seal the valve 705a in order to maintain the fluid within fluid chamber 703, conduit 701c, and balloon 702.

Moreover, pressure-sensing module 720 includes a pressure-sensing membrane 704 coupled to the fluid chamber 703, and a sensing circuitry 707 coupled to or in communication with the pressure-sensing membrane 703, said sensing circuitry 707 configured to detect a pressure applied to the uterine balloon 702 of the catheter 701.

Figure 8A:
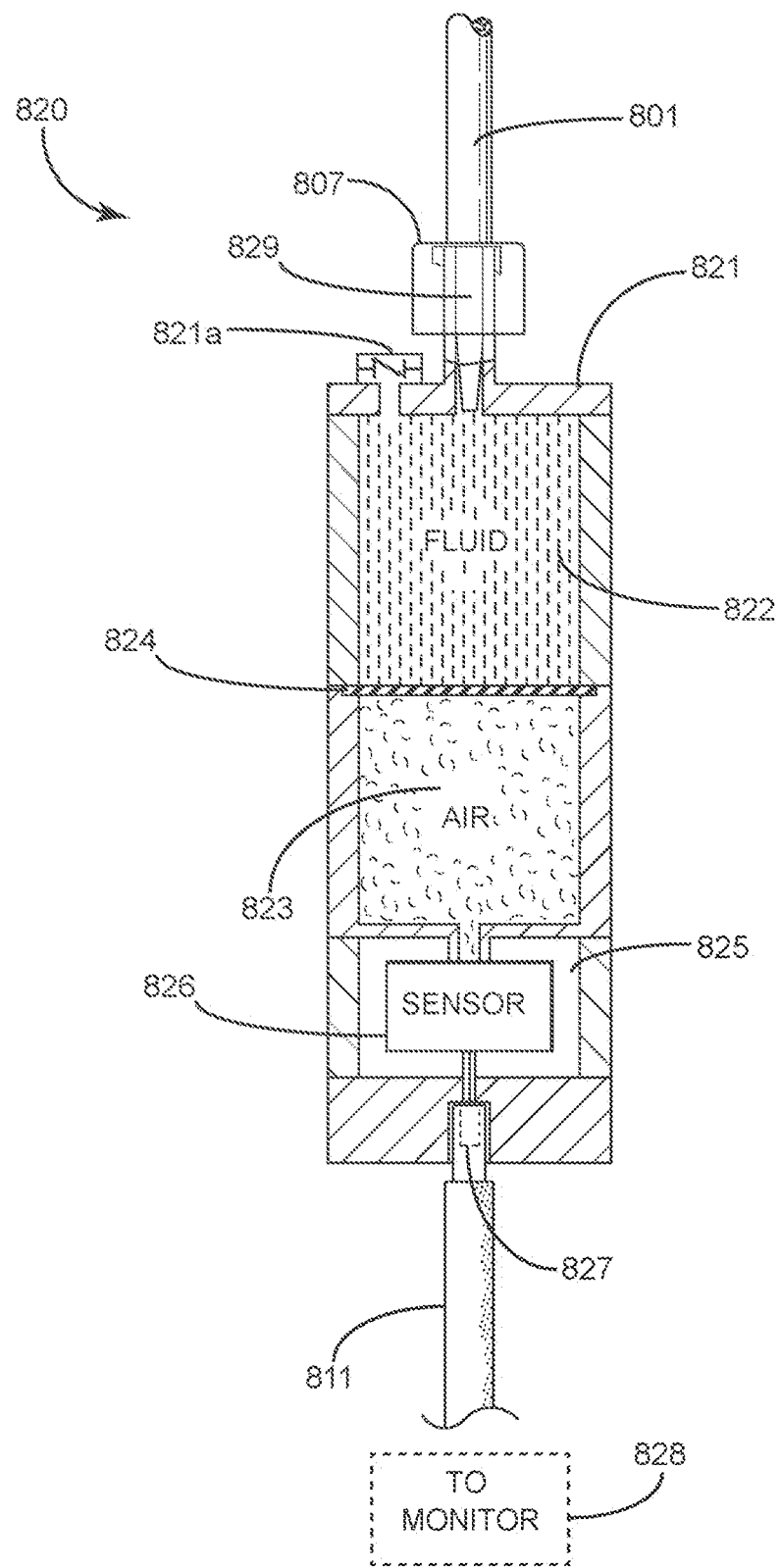
FIG. 8A illustrates an exemplary pressure sensing module in accordance with some embodiments of the present invention.

Now turning to the next set of figures, FIG. 8A illustrates an exemplary pressure sensing module 820 in accordance with some exemplary embodiments of the present invention. In the shown embodiment, the pressure sensing module 820 includes an enclosure 821 having a valve 821a, first chamber 822 in fluid communication with the conduit 829, a second chamber 823 in fluid communication with a sensor 826, and an pressure-sensing membrane 824 separating the first chamber 822 from the second chamber 823, wherein the pressure sensing module 820 is configured to detect a pressure applied to the balloon 810 of the catheter 801. In some exemplary embodiments, such as the one depicted in FIG. 8A, the second chamber 822 of the pressure sensing module 820 houses a second fluid that is distinct from the fluid introduced through the first port 806 into the first chamber 822. In some exemplary embodiments, the fluid in the second chamber 823 is a gas or a liquid. In some exemplary embodiments, a gas in the second chamber may be simply air. In some exemplary embodiments, the fluid introduced through the first port 806 into the first chamber 822 is water or a nontoxic liquid.

Figure 8B:
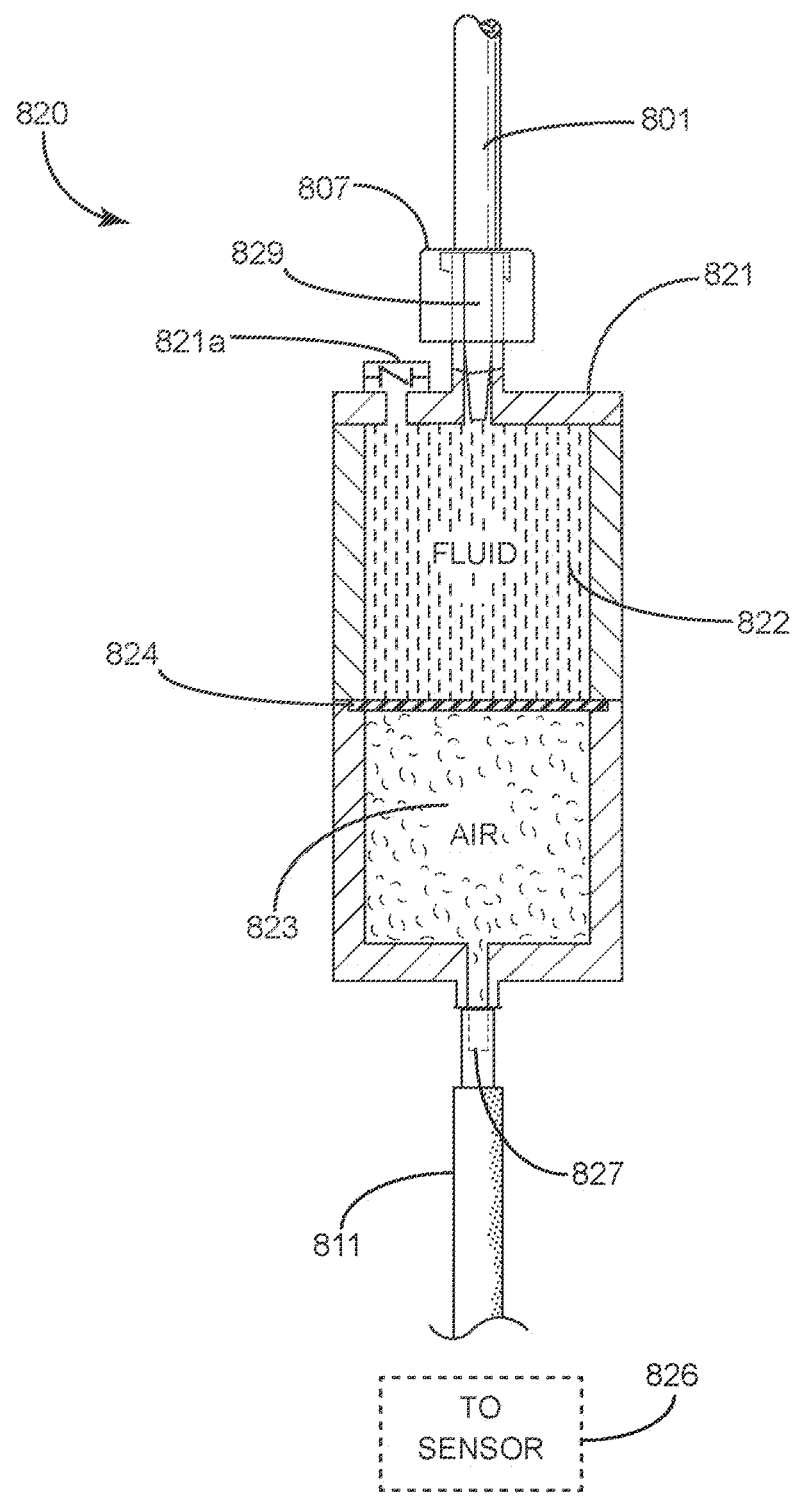
FIG. 8B illustrates an exemplary pressure sensing module in accordance with some embodiments of the present invention.

Now turning to the next figure, FIG. 8B illustrates pressure sensing module 820 in accordance with some exemplary embodiments of the present invention. In embodiments such as the one depicted in this figure, a pressure sensing module 820 for monitoring and measuring a change in intrauterine pressure during labor, without rupturing the amniotic sac, may include an enclosure 821 configured to couple to a first port 807 of a catheter 801, the catheter 801 including: a distal end 803 adapted to be placed at least partially inside a cervix of a patient; a balloon 810 situated substantially at the distal end 803 of the catheter adapted to be placed at least partially inside a uterus of the patient; a second port 806 situated at the proximate end 802 of the catheter 801; and a conduit fluidly communicating the second port 806 and the first port 807 to an interior of the balloon 801, wherein the balloon 801 is inflated by introducing a fluid through the second port 806; a first chamber 822 housed within the enclosure 821 and in fluid communication with the conduit; a second chamber 823 housed within the enclosure 821 and in fluid communication with a sensor 826; and an pressure-sensing membrane 824 separating the first chamber 822 from the second chamber 823, wherein the sensor 826 is configured to detect a pressure applied to the balloon 810 of the catheter 801. In the shown embodiments, air that may be occupying chamber 822 prior to a liquid being introduced, may be ejected out of chamber 822 via a valve 821a.

In some exemplary embodiments, the pressure sensing module 820 may include a second chamber 823 that houses a second fluid that is distinct from the fluid introduced through the second port 806 into the first chamber 822. In some embodiments, the fluid in the second chamber 823 is a gas or a liquid. In some exemplary embodiments, the gas in the second chamber 823 is air.

In some exemplary embodiments, the enclosure 821 of the pressure sensing module 820 includes a third chamber 825 for housing the sensor 826. In some exemplary embodiments, the enclosure 821 is removably coupled to the sensor 826, wherein the sensor 826 is situated external to the enclosure 821.

Now turning to the next figure, FIG. 8C illustrates pressure sensing module 820 in accordance with yet another exemplary embodiment of the present invention. In embodiments such as the one depicted in this figure, a pressure sensing module 820 for monitoring and measuring a change in intrauterine pressure during labor, without rupturing the amniotic sac, may include a second chamber 823 configured to house the sensing circuitry 826, which is coupled to the pressure-sensing membrane 824 without any interface fluid in-between. In some exemplary embodiments, sensing circuitry 826 may employ transmitters or transceivers and the like to communicate with a remote monitor or monitoring device 828.

In some exemplary embodiments, sensing circuitry 826 may comprise one or more sensors adapted to generate sensing signals concerning a pressure applied to the pressure-sensing membrane 824. The sensors may include optical sensors, strain gauges, capacitive sensors, Hall Effect sensors, and the like, and may measure stress and/or strain and/or deflection of the pressure-sensing membrane 824.

Monitoring device 828 may facilitate presenting sensing data including but not limited to changes in the intrauterine pressure of a patient in labor, which may be monitored before rupturing the amniotic sac. As briefly mentioned above, an advantage of monitoring intrauterine pressure without rupturing the amniotic sac is a decrease in the ration of intrauterine infections for the mother and fetus during labor. Moreover, a monitoring device 828 may facilitate recording of the number of contractions and visually appreciating contraction patters that will be useful t the operator during the patient's labor.

Figure 9:
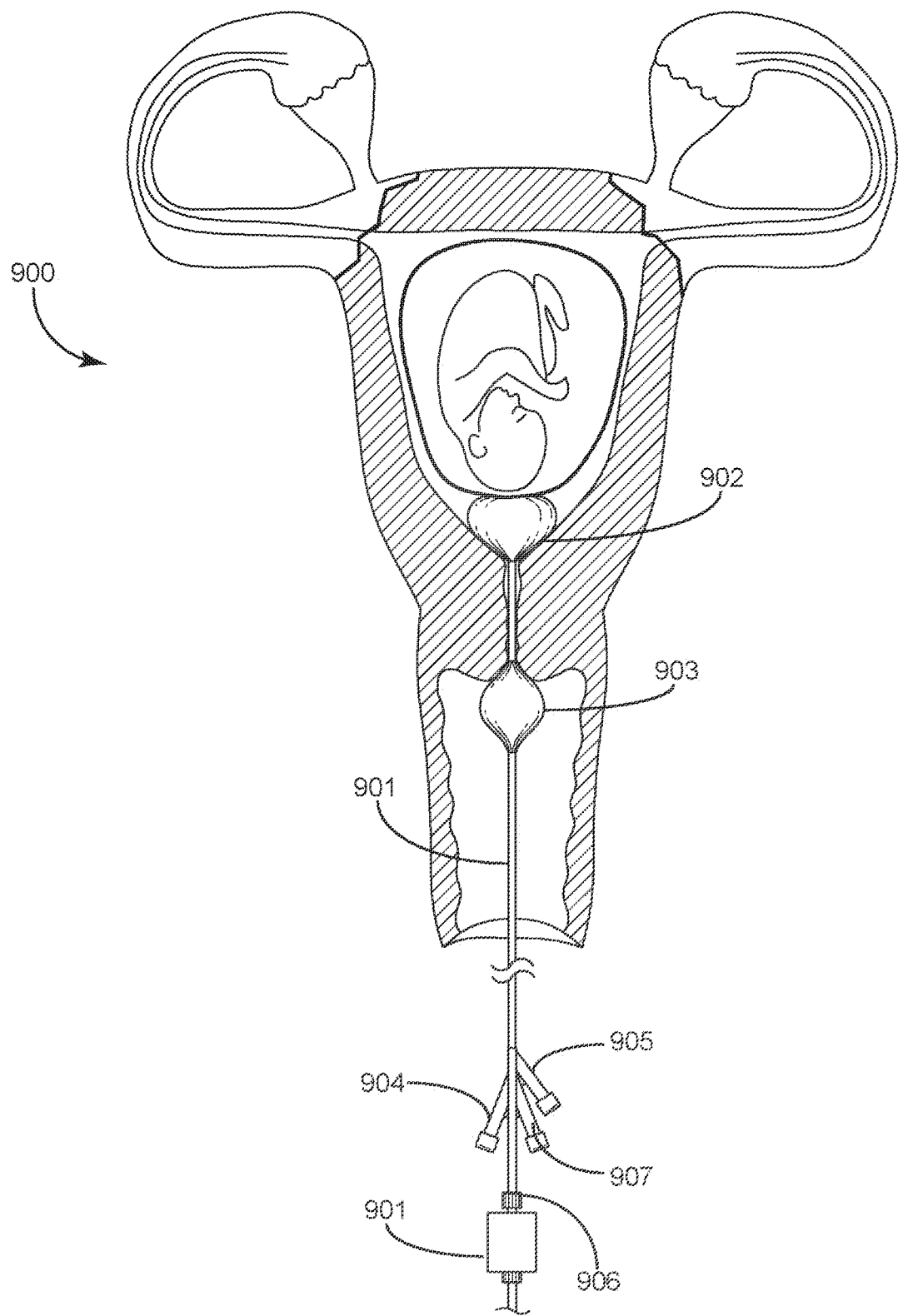
FIG. 9 illustrates an exemplary multi-balloon catheter system in accordance with the present invention, shown inside a woman's reproductive system.

Turning now to the next figure, FIG. 9 illustrates an exemplary multi-balloon catheter system in accordance with the present invention, shown inside a woman's reproductive system. More specifically, FIG. 9 depicts system 900, comprising: a catheter 901 including a uterine balloon 902, as well as a vaginal balloon 903 situated below or closer to the proximate end of the catheter than the uterine balloon and adapted to secure the uterine balloon inside the uterus; more specifically vaginal balloon 903 secures catheter 901 so that uterine balloon 902 may be more stable in its position in the lower section of the uterus. Moreover, catheter 901 includes several ports. In the embodiment shown in FIG. 9, catheter 901 includes ports 904, 905, 906, and 907.

Port 904 may, for example and in no way limiting the scope of the present invention, fluidly communicate with a conduit within catheter 901 that may be used by an operator for inserting a stylet that guides the catheter into cervix of the patient. Port 905 may, for example and in no way limiting the scope of the present invention, fluidly communicate with a conduit that fluidly connects port 905 to port 906 via an interior of the uterine balloon 902, in a manner such that injecting a fluid into port 906 may inflate balloon 902 as well as reach a chamber within pressure-sensing module 901 fluidly coupled to port 906. Port 907 may, for example and in no way limiting the scope of the present invention, fluidly communicate with vaginal balloon 903 so that injecting a fluid via port 907 will inflate vaginal balloon 903.

In some exemplary embodiments, system 900 comprises: a catheter 901 configured for manipulation by an operator, the catheter including: a distal end adapted to be placed at least partially inside a cervix of a patient; a uterine balloon 902 situated substantially at the distal end of the catheter 901 adapted to be placed at least partially inside a uterus of the patient; a vaginal balloon 903 situated closer to the proximate end of the catheter 901 than the uterine balloon 902 and adapted to secure the uterine balloon 902 inside the uterus; a first port 905, a second port 906, a third port 907, and a fourth port 904 situated at the proximate end of the catheter, wherein the third port 907 is in fluid communication with the vaginal balloon 903; and a conduit fluidly communicating the first port 905 and the second port 906 to an interior of the uterine balloon 902, wherein the uterine balloon 902 is inflated by introducing a fluid through the first port 905; and a pressure sensing module coupled to the second port 906, the pressure-sensing module including an enclosure having a chamber in fluid communication with the uterine balloon 902 via the conduit, a pressure-sensing membrane coupled to the chamber, and a sensing circuitry coupled to the pressure-sensing membrane configured to detect a pressure applied to the uterine balloon 902 of the catheter 901.

Figure 9A:
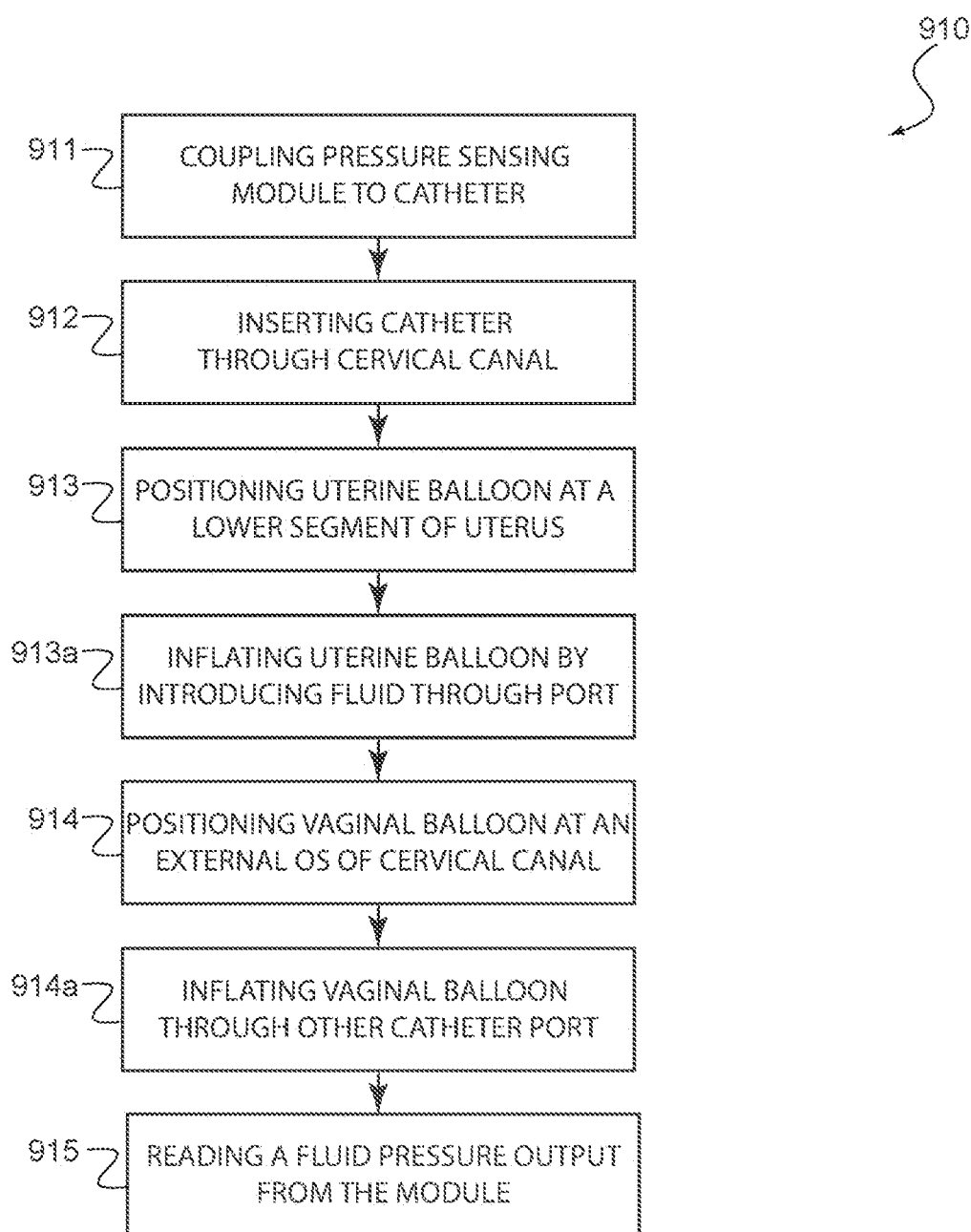
FIG. 9A illustrates an exemplary method in accordance with practice of the present invention.

A method in accordance with practice of the present invention, may include a method 910 for monitoring and measuring a change in intrauterine pressure during labor, without rupturing the amniotic sac. With reference to FIG. 9 and FIG. 9A, by way of example and in no way limiting the scope of the present invention, such method 910 may include the following steps, disclosed in one particular sequence although other sequences may be practiced without limiting from the scope of the present invention.

In step 911, a pressure-sensing module may be coupled to a catheter as described above.

In step 912, the catheter may be inserted into a vagina and through a cervical canal of a female patient, wherein a distal end of the catheter is placed inside the cervical canal, and a proximal end of the catheter is kept outside the cervical canal, the catheter including: a uterine balloon in fluid communication with the proximal end and attached at or near the distal end of the catheter, a first port situated at the proximate end of the catheter, a second port situated at the proximate end of the catheter, a conduit fluidly communicating the first port and the second port to an interior of the uterine balloon, and a vaginal balloon situated closer to the proximate end of the catheter than the uterine balloon and adapted to secure the uterine balloon inside the uterus.

In step 913, the uterine balloon may be positioned at a lower segment of a uterus of the female patient. In exemplary embodiments, subsequent to positioning the uttering balloon at the lower segment of a uterus of the female patient, at step 913a, the uterine balloon may be inflated from the proximal end and through the catheter by introducing a fluid through the first port of the catheter so that the fluid inflates the balloon and enters a first chamber of the pressure-sensing module.

In step 914, the vaginal balloon may be positioned at an external OS of the cervical canal of the female patient, prior to inflating the vaginal balloon. Subsequently, at step 914a, the vaginal balloon may be inflated to anchor the uterine balloon inside the lower segment of the uterus so that the uterine balloon rests against an amniotic sac of the female patient.

In step 915, once the vaginal balloon is secured and the uterine balloon is anchored or secured in place against the amniotic sac of the female patient—as discussed above—a pressure output may be read from the pressure-sensing module, which detects a change in intrauterine pressure or a change in pressure inside the unruptured amniotic sac, without having to rupture the amniotic sac.

In some exemplary embodiments, during or after the procedure or after taking several readings, it may be desirable to take additional measurements with instruments or devices that may be introduced through the catheter. For example, and in no way limiting the scope of the present invention, temperature transducers or imaging transducers may be inserted through an opening at the distal end of the catheter.

Figure 10:
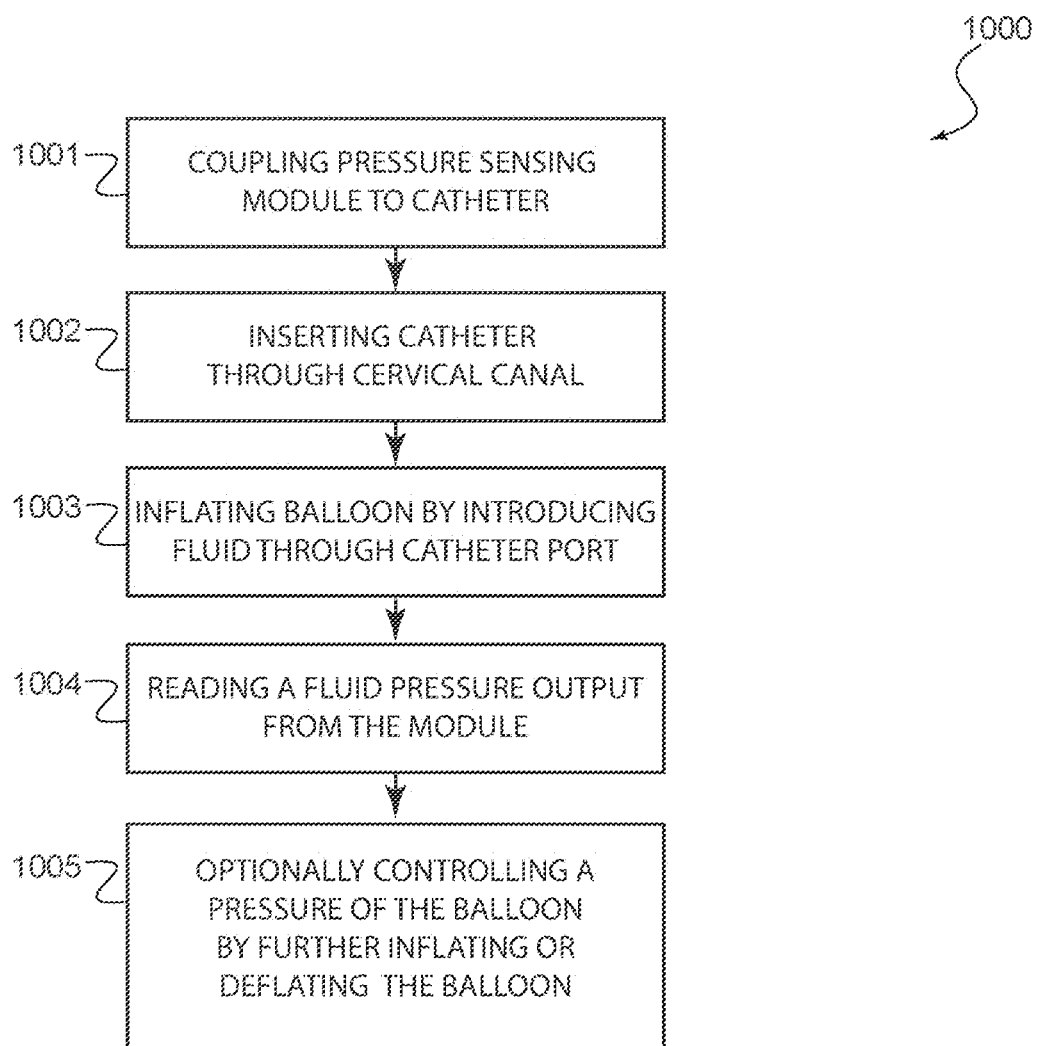
FIG. 10 illustrates an exemplary method in accordance with practice of the present invention.

Turning now to the last figure, FIG. 10 depicts another flow chart of a method in accordance with practice of the present invention. More specifically, FIG. 10 depicts method 1000, for monitoring and measuring a change in intrauterine pressure during labor, without rupturing the amniotic sac. Although method 1000 is exemplarily shown with a series of steps in one particular sequence, method 1000 may include fewer or more steps in alternative sequences without deviating from the scope of the present invention.

In exemplary embodiments, a method for monitoring and measuring a change in intrauterine pressure during labor, without rupturing the amniotic sac, may include steps 1001-1005. In exemplary embodiments, step 1001 may include coupling a pressure sensing module to a catheter.

Step 1002 may include inserting the catheter into a vagina and through a cervical canal of a female patient, wherein: a distal end of the catheter is placed inside the cervical canal, and a proximal end of the catheter is kept outside the cervical canal, the catheter including: a balloon in fluid communication with the proximal end and attached at or near the distal end of the catheter, a first port situated at the proximate end of the catheter, a second port situated at the proximate end of the catheter, and a conduit fluidly communicating the first port and the second port to an interior of the balloon. In some exemplary embodiments, the catheter may include a plurality a plurality of balloons and accordingly this step may further include: a first balloon is placed inside the uterus, and a second balloon is placed inside the vagina. In some exemplary embodiments, the catheter may include a plurality a plurality of balloons and accordingly this step may further include: a first balloon is placed inside the uterus, a second balloon is placed inside the vagina, and a third balloon is placed inside the cervical canal.

In exemplary embodiments, step 1003 may include inflating the balloon from the proximal end and through the catheter by introducing a fluid through a first port of the catheter so that the fluid enters inflates the balloon and enters a first chamber of the sensing module.

In exemplary embodiments, step 1004 reading a pressure output from the pressure sensing module.

In exemplary embodiments, step 1005 optionally controlling a pressure of the balloon by further inflating or deflating the balloon. In some exemplary embodiments, this step may comprise manually inflating or deflating the balloon. In some exemplary embodiments, this step may comprise automatically inflating or deflating the balloon, by for example implementation of a pump device.

As mentioned above, the presented embodiments disclose an inflatable system that may use a single uterine balloon, a uterine balloon and a vaginal balloon, or a uterine and a vaginal and a cervical balloon, or any combination thereof. In various embodiments, each of the named balloons (vaginal, uterine, cervical) may itself be a combination of several balloons. In some embodiments the uterine balloon and/or the cervical balloon are inflated by incompressible fluids, such as water or oil, to transfer the intracorporeal pressures to extracorporeal pressure sensors. While fluid is the best medium for transfer of pressure throughout the system, air or other gases may also be used for this purpose. In all applications, nontoxic liquids or gases are preferable.

The balloons, which may have rough external surfaces in order to keep them anchored in place, may be inflated by the operator or by the patient herself. Various sensors and other instruments may be used along with or as a part of the inflatable system to monitor cervical dilation, fetal well-being, and the woman's conditions. The disclosed inflatable system is not limited in its application to the details of construction and the arrangement of the components set forth in this specification or illustrated in the drawings.

A system and method for child-bearing monitoring and assistance has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. A pressure-sensing module comprising:
    an enclosure housing a first chamber and a second chamber, the first chamber and the second chamber separated by a pressure-sensing membrane, a sensing circuitry configured to measure a sensing data from the pressure-sensing membrane;
    wherein:
        the first chamber comprises a first fluid, the first chamber configured to fluidly-connect to a first conduit in fluid communication with a uterine balloon filled by the first fluid;
        the second chamber comprises a second fluid;
        the first fluid in the first chamber is distinct from the second fluid in the second chamber;
        the sensing circuitry measures the sensing data relating to a pressure exerted by the first fluid in the first chamber on both the pressure-sensing membrane and the second fluid of the second chamber; and
        the pressure-sensing module is configured to measure the sensing data without needing to rupture an amniotic sac.

2. The pressure-sensing module of claim 1, further comprising a communications device configured to transmit the sensing data to a remote device.

3. The pressure-sensing module of claim 2, wherein the pressure-sensing module is removably coupled to the sensing circuitry, the sensing circuitry situated external to the pressure-sensing module.

4. The pressure-sensing module of claim 1, wherein the enclosure further comprises a third chamber housing the sensing circuitry,
    wherein the sensing circuitry transmits a recorded data regarding the pressure applied to a monitor device located outside the enclosure.

5. The pressure-sensing module of claim 1, further comprising a valve, the valve configured to allow any air inside the first chamber to exit the pressure-sensing module as the first fluid is received in the first chamber.

6. The pressure-sensing module of claim 1, wherein the sensor sensing circuitry is selected from the group consisting of: an optical sensor, a strain gauge, a capacitive sensor, and a Hall Effect sensor.

7. The pressure-sensing module of claim 2 further comprising:
    a microcontroller having a memory including a set of executable instructions for reading the sensing data from the pressure-sensing module;
    wherein the sensing circuitry is configured to transmit the sensing data.

8. The pressure-sensing module of claim 7, further comprising the remote device configured to receive the sensing data from the communications device, the remote device comprising a transceiver.

9. The pressure-sensing module of claim 1, wherein the pressure-sensing membrane is impermeable.

10. The pressure-sensing module of claim 1, wherein the second fluid is a gas.

11. The pressure-sensing module of claim 10, wherein the gas is air.

12. The pressure-sensing module of claim 1, wherein the second fluid is a liquid.

13. A pressure-sensing module comprising:
    an enclosure housing a first chamber and a second chamber, the first chamber and the second chamber separated by a pressure-sensing membrane, a sensing circuitry configured to measure a sensing data from the pressure-sensing membrane;
    wherein:
        the first chamber comprises a first fluid, the first chamber configured to fluidly-connect to a first conduit in fluid communication with a uterine balloon filled by the first fluid;
        the second chamber comprises the sensing circuitry;
        the sensing circuitry measures the sensing data relating to a pressure exerted by the first fluid in the first chamber on the pressure-sensing membrane; and
        the pressure-sensing module is configured to measure the sensing data without needing to rupture an amniotic sac.

14. The pressure-sensing module of claim 13, wherein the sensing circuitry is coupled to the pressure-sensing membrane without any interference fluid in-between.

15. The pressure-sensing module of claim 13, wherein the sensing circuitry is in direct contact with the pressure-sensing membrane.

16. The pressure-sensing module of claim 13, wherein the pressure-sensing module further comprises a communications device to transmit the sensing data concerning the uterine balloon.

17. The pressure-sensing module of claim 13, wherein the pressure-sensing module is configured to transmit at least a portion of the sensing data to a monitor device located outside the enclosure.

* * * * *